United States Patent
Blacker et al.

(10) Patent No.: US 11,633,575 B2
(45) Date of Patent: Apr. 25, 2023

(54) PERCUTANEOUS DEVICE EXCHANGE

(71) Applicant: Corindus, Inc., Waltham, MA (US)

(72) Inventors: Steven J. Blacker, Framingham, MA (US); Christopher Zirps, Sharon, MA (US)

(73) Assignee: Corindus, Inc., Newton, MA (US)

( * ) Notice: Subject to any disclaimer, the term of this patent is extended or adjusted under 35 U.S.C. 154(b) by 77 days.

(21) Appl. No.: 16/491,563

(22) PCT Filed: Mar. 6, 2018

(86) PCT No.: PCT/US2018/021150
§ 371 (c)(1),
(2) Date: Sep. 5, 2019

(87) PCT Pub. No.: WO2018/165162
PCT Pub. Date: Sep. 13, 2018

(65) Prior Publication Data
US 2020/0282186 A1    Sep. 10, 2020

Related U.S. Application Data

(60) Provisional application No. 62/467,815, filed on Mar. 6, 2017.

(51) Int. Cl.
*A61M 25/09*   (2006.01)
*A61B 34/30*   (2016.01)
(Continued)

(52) U.S. Cl.
CPC ....... *A61M 25/09041* (2013.01); *A61B 34/30* (2016.02); *A61M 25/0113* (2013.01);
(Continued)

(58) Field of Classification Search
CPC ........ A61M 25/09041; A61M 25/0113; A61M 25/0169; A61M 39/06; A61M 39/28;
(Continued)

(56) References Cited

U.S. PATENT DOCUMENTS 5,318,541 A   6/1994   Viera et al.
5,572,999 A   11/1996  Funda et al.
(Continued)

FOREIGN PATENT DOCUMENTS

CN   101902990   12/2010
CN   103124531   5/2013
(Continued)

OTHER PUBLICATIONS

Extended European Search Report for Corresponding EP Application No. 18764612.
(Continued)

*Primary Examiner* — Richard G Louis

(57) ABSTRACT

An apparatus includes a hemostasis valve; a base having a clamp releasably coupling a catheter to the base; a base drive member moving the base relative to the hemostasis valve along a first path; and a mechanism maintaining the position of an elongated medical device relative to the hemostasis valve while the catheter is being moved along the first path.

28 Claims, 17 Drawing Sheets

(51) Int. Cl.
*A61M 25/01* (2006.01)
*A61M 39/06* (2006.01)
*A61M 39/28* (2006.01)

(52) U.S. Cl.
CPC ........ *A61M 25/0169* (2013.01); *A61M 39/06* (2013.01); *A61M 39/28* (2013.01); *A61B 2034/301* (2016.02); *A61M 2039/062* (2013.01)

(58) Field of Classification Search
CPC .. A61M 2039/062; A61M 2025/09125; A61B 34/30; A61B 2034/301; A61B 2017/00292; A61B 2017/0034; A61B 2034/303; A61B 17/00; A61B 17/00234
See application file for complete search history.

(56) References Cited

U.S. PATENT DOCUMENTS

| | | | |
|---|---|---|---|
| 5,849,016 A | 12/1998 | Suhr | |
| 2002/0010425 A1* | 1/2002 | Guo | A61M 39/06 604/167.04 |
| 2002/0177789 A1 | 11/2002 | Ferry et al. | |
| 2004/0034311 A1 | 2/2004 | Mihalcik | |
| 2006/0041245 A1* | 2/2006 | Ferry | A61B 90/50 604/95.01 |
| 2007/0060879 A1* | 3/2007 | Weitzner | A61M 25/1002 604/95.04 |
| 2008/0045892 A1 | 2/2008 | Ferry et al. | |
| 2010/0069833 A1* | 3/2010 | Wenderow | A61B 17/00234 604/95.01 |
| 2010/0204646 A1* | 8/2010 | Plicchi | A61B 34/30 604/95.01 |
| 2011/0092910 A1* | 4/2011 | Schultz | A61M 25/0662 604/165.04 |
| 2012/0184955 A1 | 7/2012 | Pivotto et al. | |
| 2012/0253320 A1 | 10/2012 | Steegers et al. | |
| 2013/0184805 A1 | 7/2013 | Sawada | |
| 2014/0066899 A1 | 3/2014 | Blacker et al. | |
| 2014/0148759 A1 | 5/2014 | MacNamara et al. | |
| 2014/0171919 A1 | 6/2014 | Blacker | |
| 2014/0276391 A1* | 9/2014 | Yu | A61M 25/0105 604/95.01 |
| 2014/0276939 A1 | 9/2014 | Kokish et al. | |
| 2016/0184552 A1 | 6/2016 | Hou et al. | |
| 2017/0049995 A1 | 2/2017 | Blacker | |

FOREIGN PATENT DOCUMENTS

| | | |
|---|---|---|
| CN | 103179921 | 6/2013 |
| CN | 105658164 | 6/2016 |
| CN | 105848703 | 8/2016 |
| CN | 205832390 | 12/2016 |
| EP | 2216068 | 8/2010 |
| JP | 2011519678 | 7/2011 |

OTHER PUBLICATIONS

International Search Report and Written Opinion for PCT/US2018/021150; dated May 16, 2018; 14 pages.

* cited by examiner

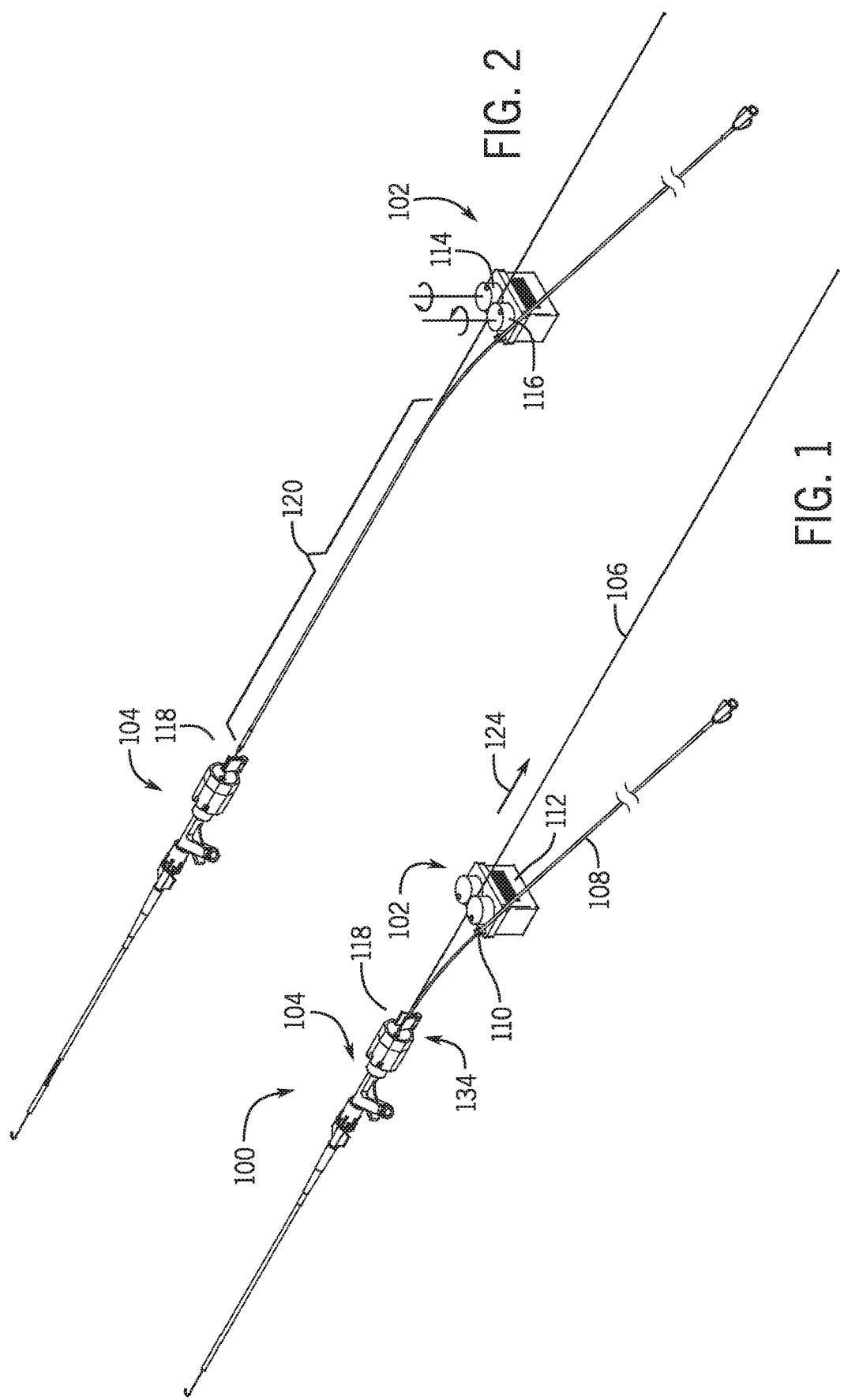

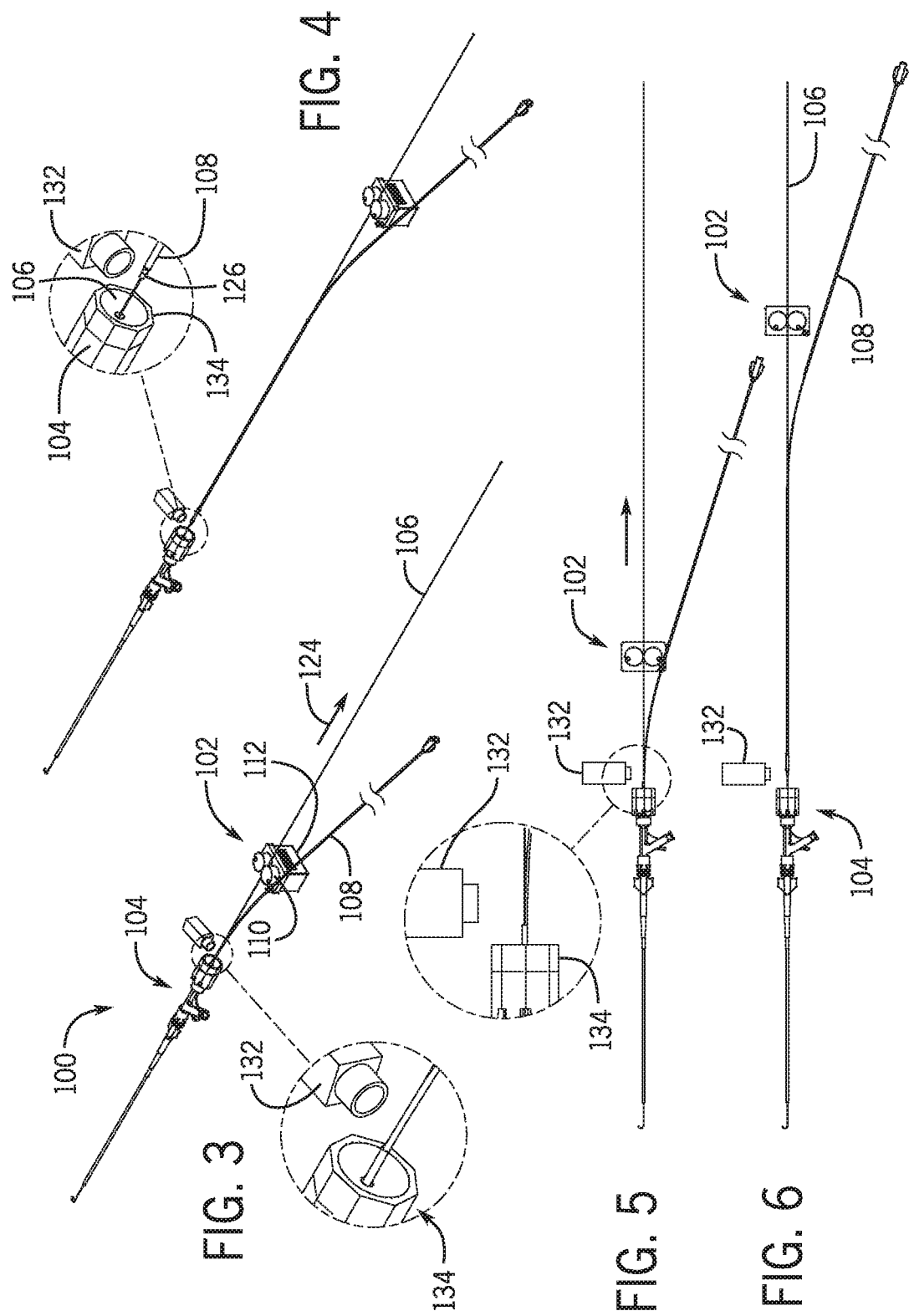

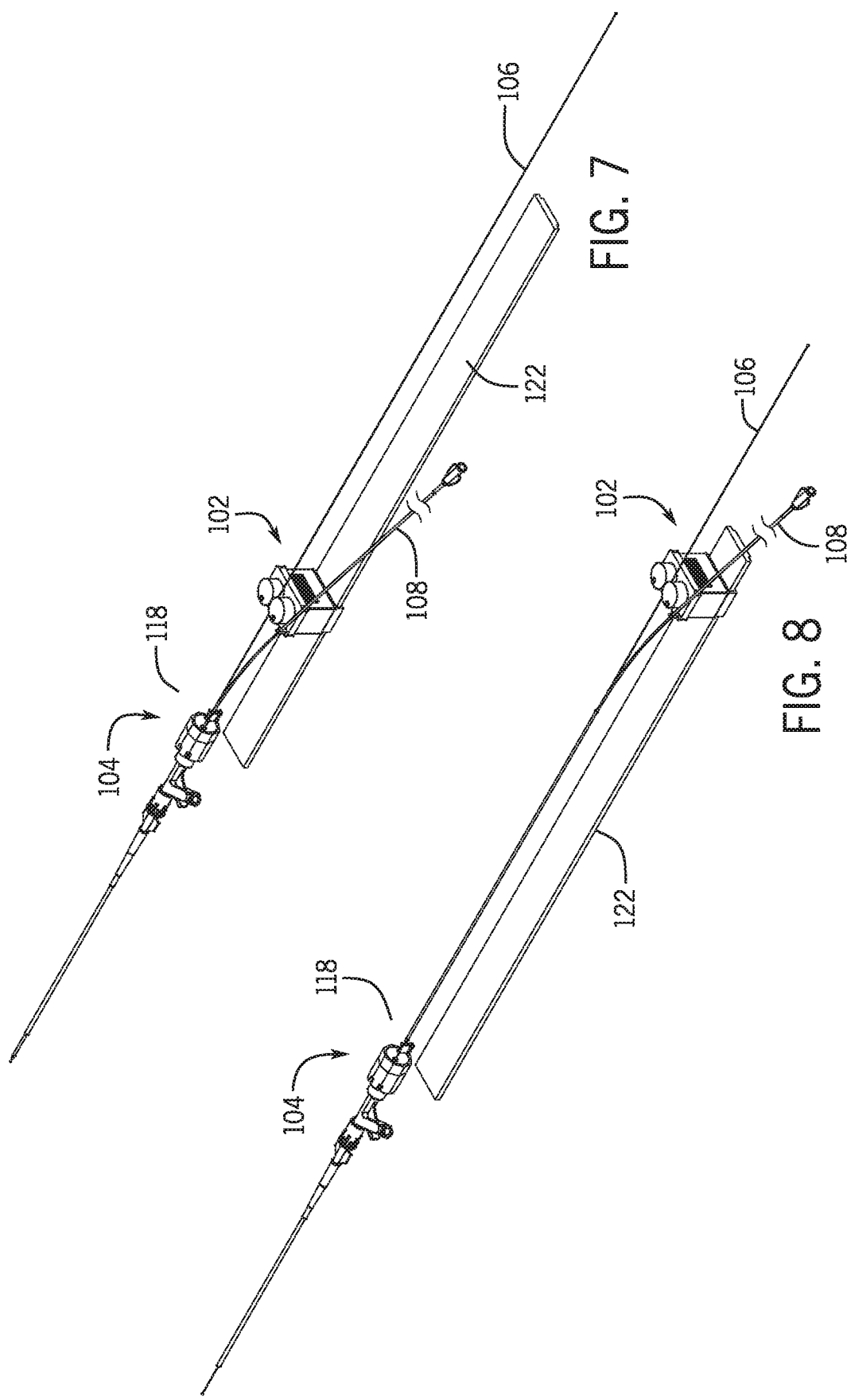

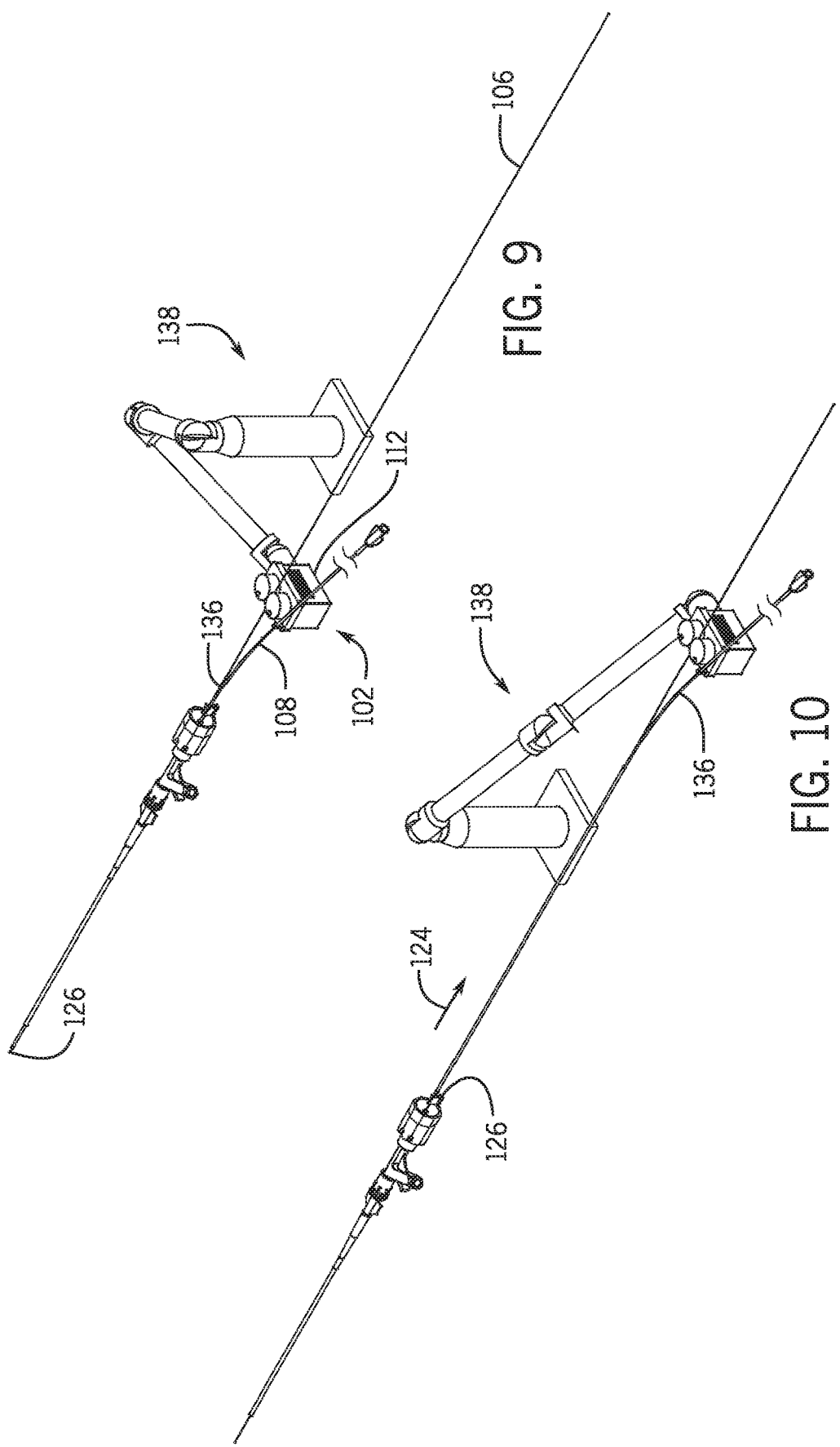

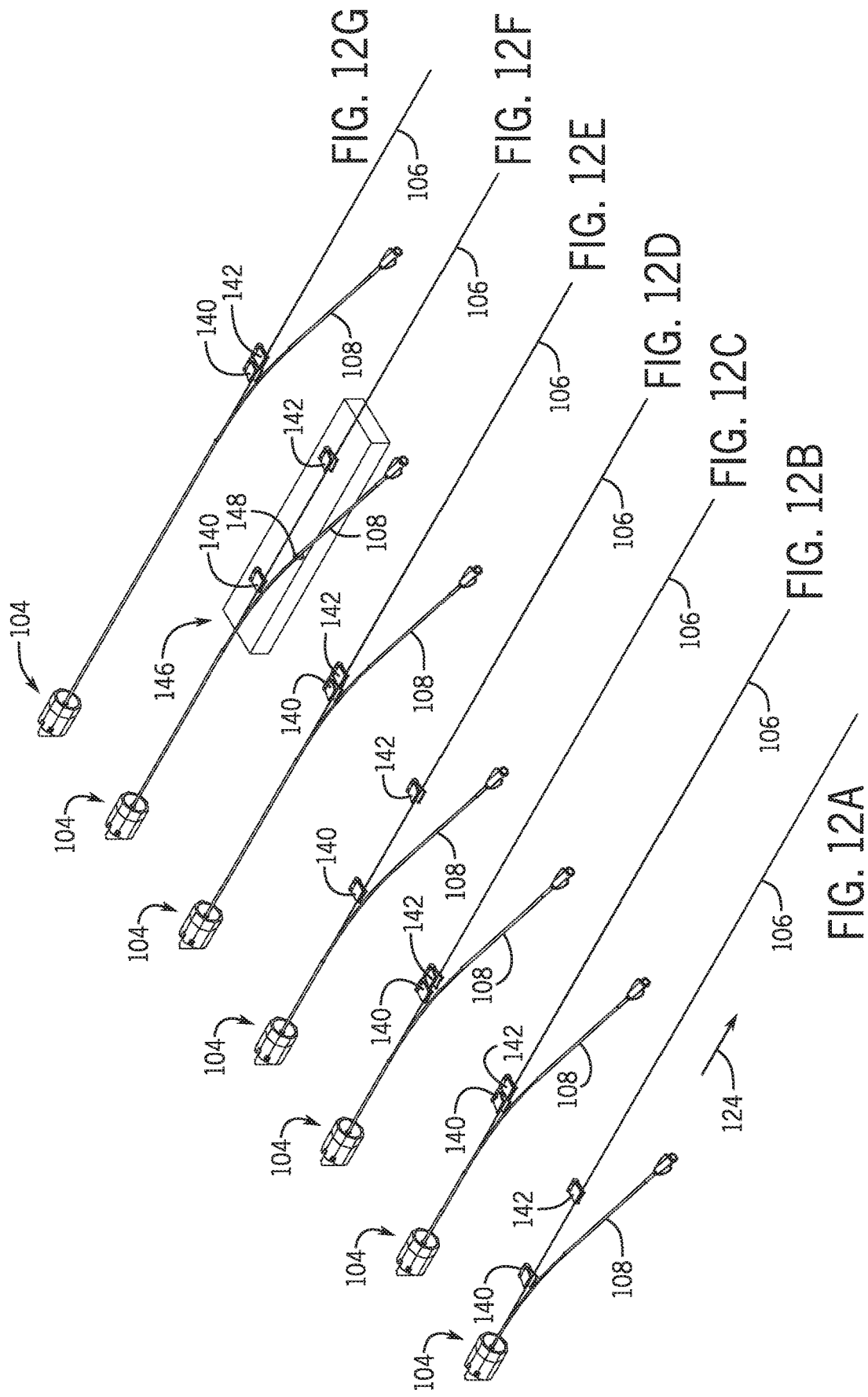

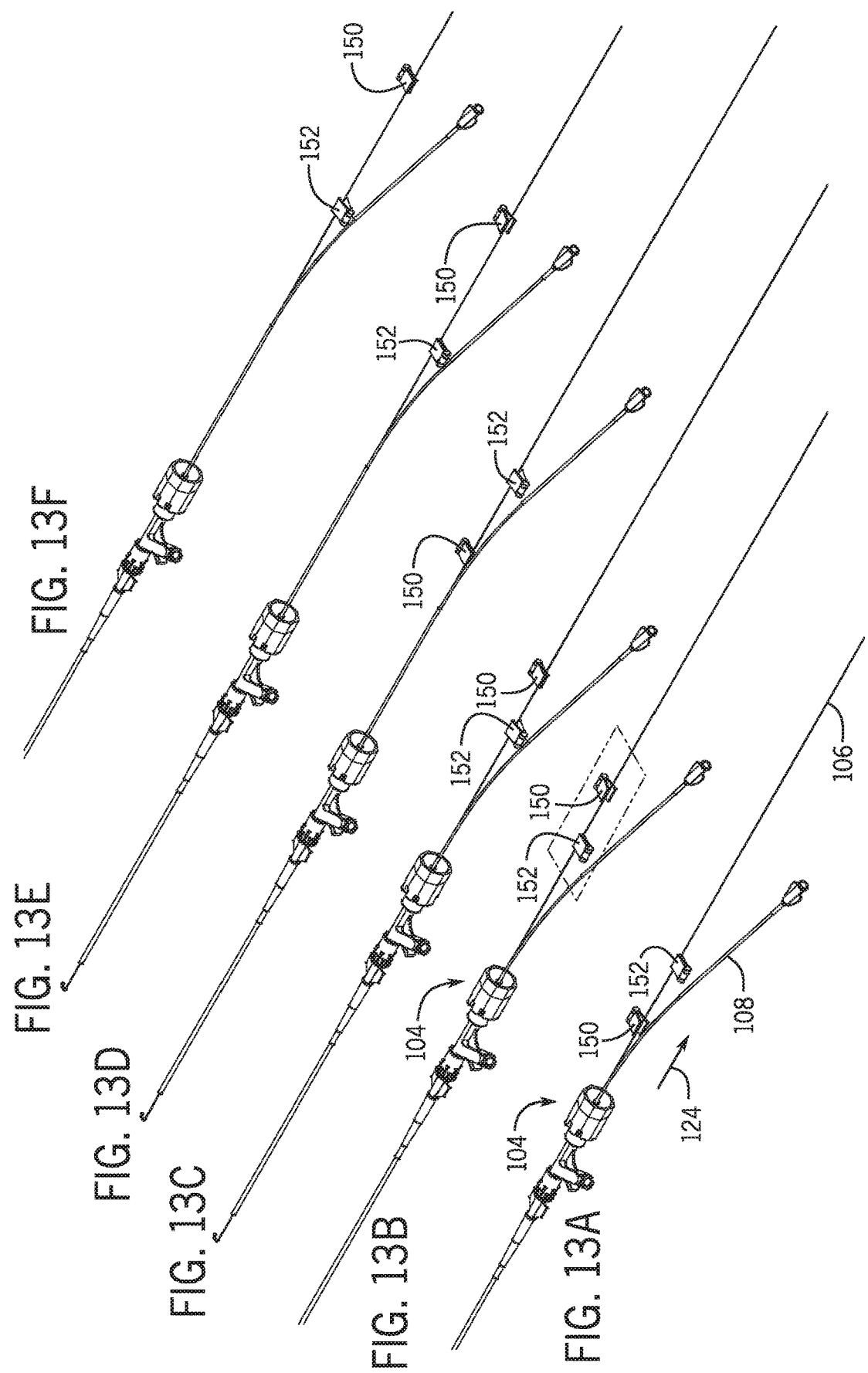

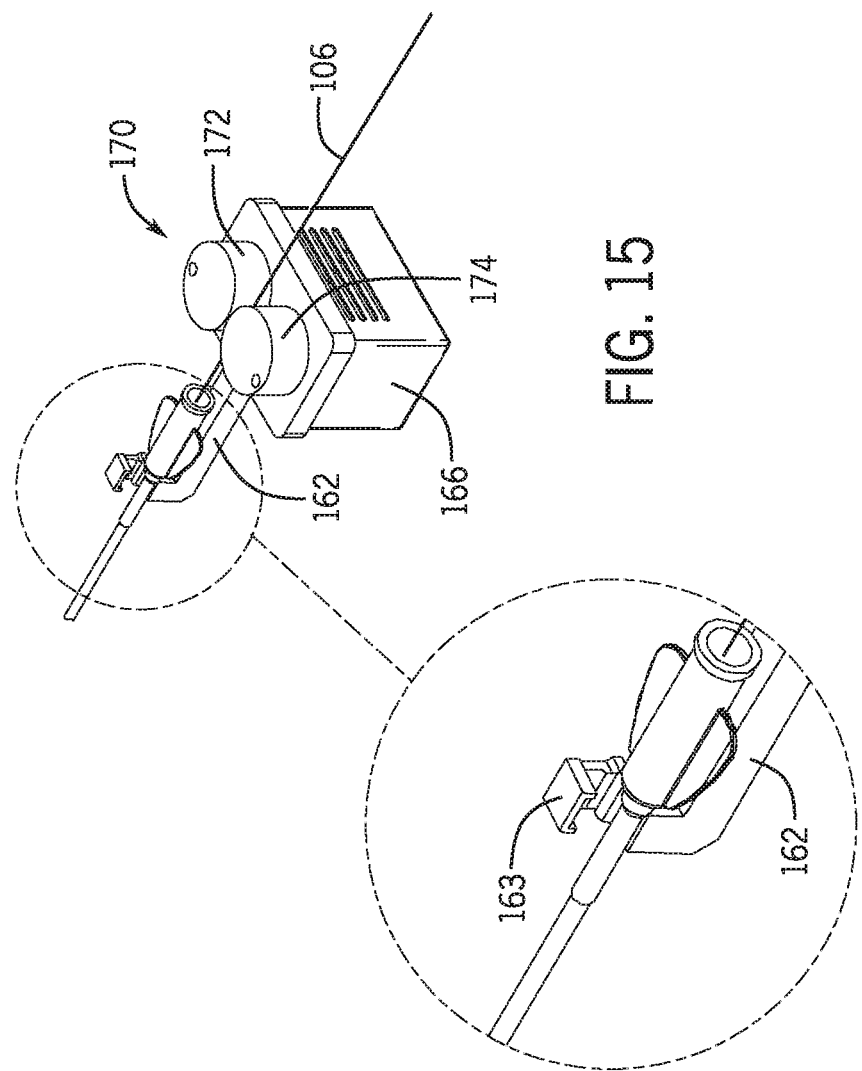
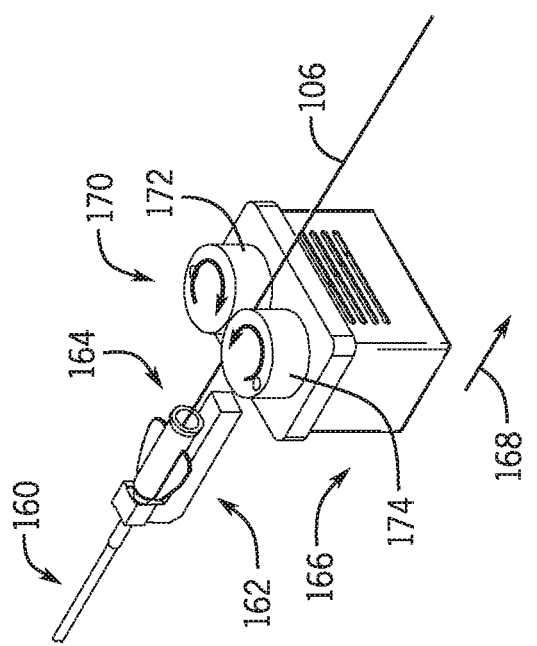
FIG. 15
FIG. 14

PERCUTANEOUS DEVICE EXCHANGE

CROSS-REFERENCE TO RELATED PATENT APPLICATIONS

This application claims the benefit of U.S. Provisional Application No. 62/467,815 filed on Mar. 6, 2017 and entitled Percutaneous Device Exchange and incorporated herein by reference in its entirety.

BACKGROUND

The present invention relates generally to the field of robotic percutaneous device systems and more particularly, to a system for exchanging percutaneous devices.

Vascular disease, and in particular cardiovascular disease, may be treated in a variety of ways. Surgery, such as cardiac bypass surgery, is one method for treating cardiovascular disease. However, under certain circumstances, vascular disease may be treated with a catheter based intervention procedure, such as angioplasty. Catheter based intervention procedures are generally considered less invasive than surgery.

During one type of intervention procedure, a guide catheter is inserted into a patient's femoral artery through an introducer and positioned proximate the coronary ostium of a patient's heart. A guidewire is inserted into the guide catheter typically through a hemostasis valve and maneuvered through the patient's arterial system until the guidewire reaches the site of the lesion. A percutaneous device is then moved along the guidewire until the device such as a balloon and stent is positioned proximate the lesion to open a blockage to allow for an increased flow of blood proximate the lesion. In addition to cardiovascular disease, other diseases may be treated with catheterization procedures.

Percutaneous devices are often exchanged during a procedure. For example, during a procedure a balloon catheter may be guided to a lesion along a guidewire pre dilatation. The balloon catheter is then removed, and a stent catheter is guided to the lesion along the guidewire post dilatation.

SUMMARY

In one embodiment an apparatus includes a hemostasis valve; a base having a clamp releasably coupling a catheter to the base; a base drive member moving the base relative to the hemostasis valve along a first path; and a mechanism maintaining the position of an elongated medical device relative to the hemostasis valve while the catheter is being moved along the first path.

In a further embodiment a portion of the elongated medical device is removably positioned within a lumen of the catheter.

In a further embodiment the first path is a direction that is substantially parallel to both a longitudinal axis of the elongated medical device and a longitudinal axis of the catheter.

In a further embodiment a distal portion of the elongated medical device is maintained in a substantially fixed location relative to an anatomical feature within a patient as the base moves in the first direction, and wherein the distance between the distal portion of the elongated medical device and the base changes as the base moves along the first path.

In a further embodiment at least a portion of the first path is linear.

In a further embodiment at least a portion of the first path is not-linear.

In a further embodiment the base moves along the elongated medical device as the base moves in the first direction.

In a further embodiment the mechanism includes a discrete movement drive mechanism that moves the elongated medical device relative to the base in a series of discrete distances.

In a further embodiment the base drive member moves the base with one or more degrees of freedom.

In a further embodiment the base drive member is being moved by a robotic arm having one or more degrees of freedom.

In a further embodiment the robotic arm moves the base relative to an access site of a patient.

In a further embodiment the robotic arm moves the base relative to a position on a patient bed.

In a further embodiment the catheter is a rapid exchange device having a monorail portion having a lumen therein for a fixed length, the elongated medical device being movably received in the lumen of the monorail portion.

In a further embodiment a distal clamp is removably clamping a portion of the elongated medical device once a distal end of the monorail portion of the catheter is between the distal clamp and the base.

In a further embodiment the distal clamp is positioned between the hemostasis valve and the base.

In a further embodiment the elongated medical device is free to move relative to the mechanism when the distal clamp clamps the elongated medical device thereto.

In a further embodiment the elongated medical device is removed from the monorail by an elongated medical device removal drive that moves the elongated medical device through the monorail in a second direction such that the proximal end of the elongated medical device is pulled through the monorail toward the hemostasis valve.

In a further embodiment the mechanism includes a pair of wheels operatively moving the elongated medical device relative to the base.

In a further embodiment the mechanism includes a first clamp member and a second clamp member moving in direction away from the hemostasis valve.

In a further embodiment the first clamp member moves from a first position where the first clamp is intermediate the second clamp and the hemostasis valve and to a second position where the second clamp is intermediate the first clamp and the hemostasis valve.

In a further embodiment the elongated medical device is a guidewire.

In a further embodiment the catheter is an over the wire device having a lumen extending from a proximal end to a distal end of the catheter, the elongated medical device being movably received in the lumen.

In a further embodiment a portion of the elongated medical device is maintained in a substantially fixed location relative to the hemostasis valve as the base moves in the first direction, and wherein the distance between the portion of the elongated medical device and the base changes as the base moves along the first path.

In a further embodiment the catheter is positioned within a hemostasis valve directly without being in a lumen of another catheter device in the hemostasis valve.

In a further embodiment a second hemostasis valve is positioned such that a first hemostasis valve is intermediate the base and the second hemostasis valve.

In one embodiment an apparatus for loading an elongated medical device through a lumen of a catheter includes a catheter support positioning a distal end of a catheter having a catheter lumen; and a drive moving the elongated medical device relative to the catheter inserting a proximal end of the elongated medical device into a distal opening of the catheter lumen.

In a further embodiment the drive moves the proximal end of the elongated medical device to exit through a proximal end of the catheter lumen.

In a further embodiment, the catheter support and drive are moveably positioned between an in-use position and a non-use position.

In a further embodiment a base having a first base portion supporting a first portion of the drive and a first portion of the catheter support, and a second base portion supporting a second portion of the drive and a second portion of the catheter support.

In a further embodiment the first base portion and second base portion move along a linear path toward and away from the in-use position.

In a further embodiment the first base portion and second base move a long a non-linear path toward and away from the in-use position.

In a further embodiment the catheter support includes a plurality of regions selectively contacting portions of the catheter.

In a further embodiment the plurality of regions are movably controlled by a controller in one or more degrees of freedom.

In a further embodiment an imaging system detecting the location of the distal tip of the elongated medical device a and the proximal opening of the catheter lumen.

In a further embodiment a control system using information from the imaging system to provide instructions via a controller to position the drive and the catheter locator to align the proximal tip of the elongated medical device with the opening of the distal end of the catheter lumen.

In a further embodiment the catheter locator includes a portion configured to avoid contact with a therapeutic element positioned on the catheter.

In a further embodiment the catheter support and drive are moved between an in-use and non-use position by one of a robotic arm, linear actuator, movable base and a rotational base.

In a further embodiment the elongated medical device is a guidewire.

In one embodiment an apparatus includes a hemostasis valve; a base having a clamp releasably coupling a first catheter to the base; a base drive member moving the base relative to the hemostasis valve along a first path; a mechanism maintaining the position of an elongated medical device relative to the hemostasis valve while the catheter is being moved along the first path; a catheter support positioning a distal end of a second catheter having a catheter lumen; and an elongated percutaneous drive moving the elongated medical device relative to the second catheter inserting a proximal end of the elongated medical device into a distal opening of the catheter lumen.

In one embodiment an apparatus includes a hemostasis valve; and a loader including a catheter support positioning a distal end of a catheter having a catheter lumen; and an elongated percutaneous drive moving the elongated medical device relative to the catheter inserting a proximal end of the elongated medical device into a distal opening of the catheter lumen. An unloader includes a base having a clamp releasably coupling the catheter to the base and a base drive member moving the base relative to the hemostasis valve along a first path; the unloaded includes a mechanism maintaining the position of an elongated medical device relative to the hemostasis valve while the catheter is being moved along the first path.

BRIEF DESCRIPTION OF THE DRAWINGS

FIG. 1 is a schematic view of the exchange system in a first position.

FIG. 2 is a schematic view of the exchange system in a second position

FIG. 3 is a schematic view of the exchange system in a first position with a proximity sensor.

FIG. 4 is a schematic view of the exchange system in the second position with a proximity sensor.

FIG. 5 is a top plan schematic view of the exchange system in the first position.

FIG. 6 is a top plan schematic view of the exchange system in the first position.

FIG. 7 is a schematic view of the exchange system in the first position with a slide.

FIG. 8 is a schematic view of the exchange system in the second position with a slide.

FIG. 9 is a schematic view of the exchange system in the first position with a robotic arm.

FIG. 10 is a schematic view of the exchange system in the second position with a robotic arm.

FIG. 12A-12G are schematic views of the exchange system with a first pair of clamps in multiple positions.

FIG. 13A-13F are a schematic view of the exchange system with a second pair of clamps in multiple positions.

FIG. 14 is a schematic view of an exchange system for an over the wire catheter in a clamped position.

FIG. 15 is a schematic view of an exchange system for an over the wire catheter in an unclamped position.

DETAILED DESCRIPTION OF THE EXAMPLE EMBODIMENTS

Figure 18:
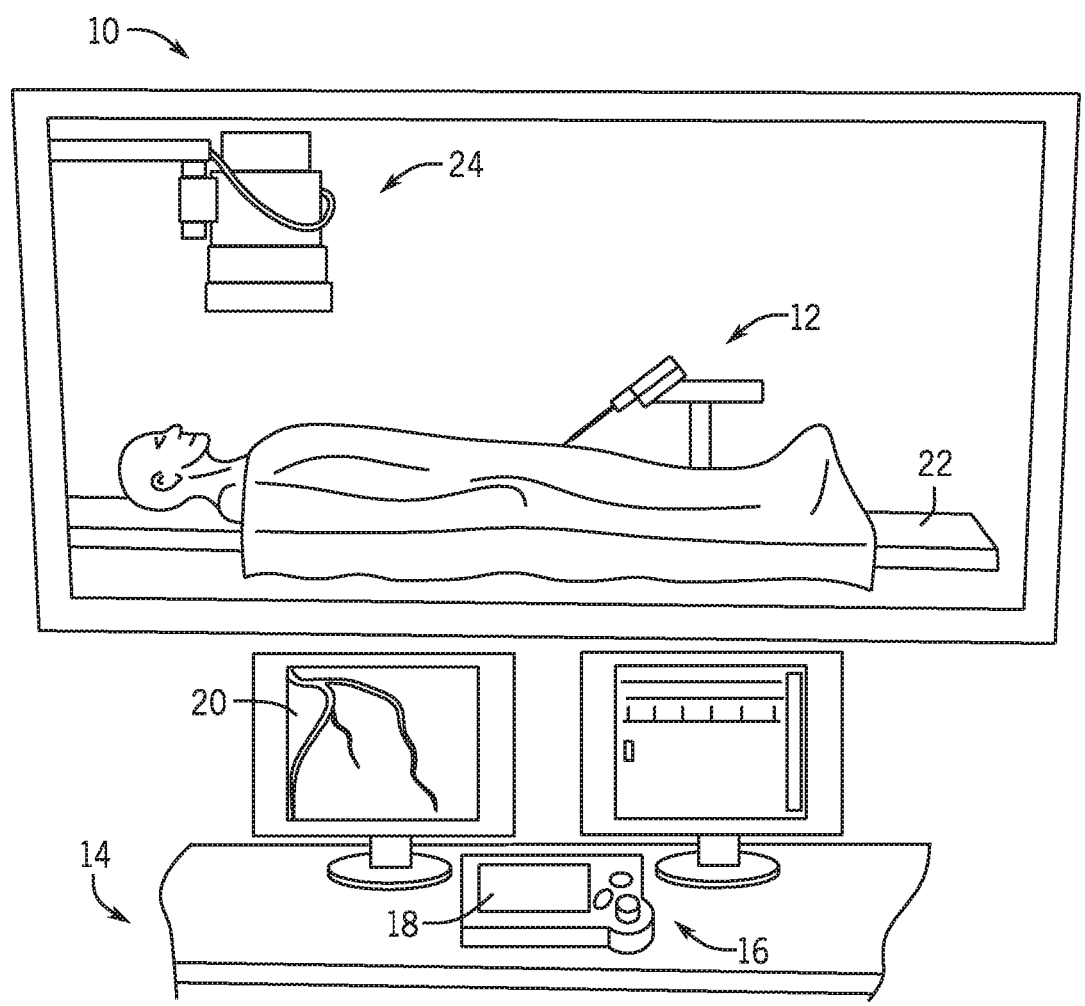
FIG. 18 is a schematic view of a robotic catheter system with a bedside unit and a remote work station.

A robotic system such as the system disclosed in U.S. application Ser. No. 15/029,115 entitled Guide Catheter Control Flexible Track which is incorporated herein by reference in its entirety permits robotic control of a guidewire, a catheter or other elongated medical device and a guide catheter. Referring to FIG. 18, robotic catheter system 10 operates proximate a patient bedside system 12 adjacent a patient bed 22. A remote work station 14 includes a controller 16, a user interface 18 and a display 20. An imaging system 24 may be any medical imaging system that may be used in conjunction with a catheter based medical procedure (e.g., non-digital x-ray, digital x-ray, CT, MRI, ultrasound, etc.). In one embodiment, imaging system 24 is a digital x-ray imaging device that is in communication with workstation 14. Imaging system 24 is configured to take x-ray images of the appropriate area of patient during a particular procedure. For example, imaging system 24 may be configured to take one or more x-ray images of the heart to diagnose a heart condition. Imaging system 24 may also be configured to take one or more x-ray images during a catheter based medical procedure (e.g., real-time images) to assist the user of workstation 14 to properly position a guidewire, guide catheter, and a working catheter such as a stent during a procedure. The image or images may be displayed on display 20 to allow the user to accurately position a distal tip of a guidewire or working catheter into proper position in a patient's vasculature. As used herein the term elongated medical device includes a guidewire, a catheter or any other elongated medical device known in the industry including but not limited to elongated percutaneous devices.

During certain catheter procedures it may be necessary to exchange one catheter device with another catheter device. As noted above, during a procedure a balloon catheter may be guided to a lesion along a guidewire. After the balloon catheter is inflated the balloon catheter is then removed and a stent catheter is guided to the lesion along the guidewire post dilatation. In one procedure during the exchange of the balloon catheter and the stent catheter the distal end of the guidewire is maintained in a position distal the lesion being treated. However other positions within the vasculature are contemplated. As the balloon catheter is being withdrawn from the vasculature it is desirable to maintain the distal end of the guidewire in a fixed position relative to a lesion or anatomical feature within the vasculature. In the over the wire catheter platform a guidewire 106 is maneuvered either manually or using a robotic drive system to drive a distal end 184 of the guidewire to or beyond a region of interest such as a lesion within a vasculature of a patient. In order to exchange the over the wire catheter the distal end 180 of an over the wire catheter 160 is slid off proximal end 186 of the guidewire 106. In an over the wire platform a proximal end of a guidewire 186 is inserted into a distal end 180 of a lumen in the catheter or percutaneous device and the catheter is slid along the guidewire along its entire length until the proximal end 186 of the guidewire extends out of the proximal opening 182 in the catheter lumen at a position at the proximal end of the catheter. The terms distal as used herein referring to a part of a component is the portion of the component that is closer to or within a vasculature during a procedure and the term proximal is the portion that is further from the vasculature when the device is being used during a vasculature procedure. The distal end is generally opposite the proximal end of the component.

In order to perform an exchange of an over the wire catheter with another over the wire catheter the guidewire needs to be longer than the length of the first catheter. guidewires used for over the wire platforms may be between 270-400 cm. In one technique an assistant applies pressure to the proximal portion of the guidewire to maintain the distal end of the guidewire in a fixed position while the catheter is being pulled off. The fixed position may be relative to one of a y-connector, a hemostasis valve, an introducer, a patient bed, a position within the vasculature, or a specific location on earth. Once the distal end of the catheter clears the patient the guidewire may be held at a position proximate the entry point of the patient to maintain the position of the distal end of the catheter in the vasculature while the catheter is fully pulled off of the proximal end of the guidewire. To load a different or even the catheter on to the guidewire an opening in the catheter lumen on the distal end of the catheter is slide over the proximal end of the guidewire.

In a rapid exchange catheter platform, a rapid exchange catheter includes a distal end having a distal opening into a guidewire receiving lumen that receives a proximal end of the guidewire. The guidewire receiving lumen extends for a set distance within the catheter and terminates at an exit port. The proximal end of the guidewire is inserted into the catheter guidewire receiving lumen and exits the exit port of the catheter. The distal end of the catheter is then driven along the guidewire until the distal end of the catheter is proximate the lesion to be treated. The distance between the opening of the guidewire receiving lumen and the exit port is referred to as the monorail portion of the catheter and may be between 20-25 cm, though other distances are contemplated.

Referring to FIG. 1 a system 100 includes a movable drive 102 that moves toward and from a y-connector 104 including a hemostasis valve 105. An elongated medical device 106 is received with drive 102 and a percutaneous device 108 such as a stent catheter is removably held on drive 102 with a holding mechanism 110 such as clamp. In one embodiment elongated medical device 106 is a guidewire. The term guidewire will be used in the description. However, it is contemplated that other elongated medical devices may also be used where the term guidewire is used.

Movable drive 102 includes a base 112 that supports holding mechanism 110. In one embodiment holding mechanism is integrally formed with base 112. Base 112 may be on a slide 122 that is robotically moved away from and toward y-connector 104. In one embodiment y-connector 104 is a hemostasis valve. Movable drive in one embodiment includes a pair of wheels 114 and 116. Wheel 114 may be a drive wheel and 116 may be a driven wheel. Drive wheel 114 is driven by a motor and controlled by a control system.

In one embodiment an operator positions a distal end of a guidewire 106 distal a lesion of a patient manually or using a robotic system such as the one described in the '115 application referenced above. System 100 is used to exchange a first percutaneous device with a second percutaneous device are guided along guidewire 106. A region near the proximal end of first percutaneous device 108 is secured to movable drive 102. In one embodiment, the distal end of the proximal shaft of the first percutaneous device 108 to be removed from the patient is secured to the holding mechanism 110 when movable drive 102 is in the first position.

Once the first percutaneous device is secured to movable drive 102 via the holding mechanism 110, the guidewire 106 is placed between wheels 114 and 116. A control system (not shown) moves the movable drive 102 to a second position (See FIG. 2) in a direction 124 away from the Y-connector 104. Simultaneous to the movement of the movable drive 102 toward the second position drive wheels 114 and 116 rotate at a speed to feed proximal portion of the guidewire toward the Y-connector. As a result, the distal end of the guidewire does not move relative to the lesion. This is accomplished by moving the guidewire toward the Y-Connector at the same rate that the movable drive base is moving away from the Y-connector.

Stated another way movable drive 102 maintains the guidewire in a nonmovable or fixed position relative to the patient as the movable drive moves from the first position to the second position. Once the monorail portion 120 of the first percutaneous device is on the side of the Y-connector distal the patient the movable drive can continue to a third position (not shown) in which the proximal terminal end of the guidewire is no longer in the movable drive and the first catheter is pulled completely off of the guidewire. At this point a second catheter device can be thread off the proximal end of the guidewire.

In one embodiment pair of wheels 114 and 116 form a proximal dynamic guidewire fixation device or a guidewire mechanism that maintains the guidewire in a fixed position as the movable drive 102 moves away from the y-connector. In one embodiment wheels 114 and 116 allow the movable drive 102 and percutaneous device 108 to move along guidewire 106 while maintaining guidewire 106 is a fixed position relative to the y-connector. However other devices are contemplated including but not limited to continuous, discrete or intermittent motion devices. For example, wheels could be replaced with one or a pair of continuous drive belts or as disclosed herein below a pair of clamp members.

Referring to FIGS. 3-6 and FIG. 7 system 100 percutaneous device 108 is moved away from the y-connector with a catheter drive (not shown). In one embodiment percutaneous device 108 is a rapid exchange device having a monorail portion 120. Monorail portion 120 is formed as part of the percutaneous device 108 and includes a distal opening 126, a lumen portion 128 and a proximal exit opening 130. Rapid exchange devices are well known in the art. The monorail portion 120 is typically 20-25 cm. However, monorail portions of other lengths may also be employed.

During a first stage of an exchange a first percutaneous device 108 may be initially withdrawn from a patient using a robotic drive mechanism as is known in the art in which a linear drive is acting on the percutaneous device 108 to move the percutaneous device away from the patient. While the linear drive acting to withdraw the percutaneous device a second guidewire linear drive may be acting on the guidewire to assist in maintaining the distal end of the guidewire in a static position by applying a counter pressure or movement to the portion of the guidewire within the guidewire linear drive to counter any movement of the guidewire resulting from friction of the monorail portion acting against the guidewire as the percutaneous device is being withdrawn. It is also contemplated that the guidewire may be rotated as the percutaneous device 108 is being withdrawn to assist in maintaining the position of the distal end of the guidewire in the vasculature.

Figure 11:
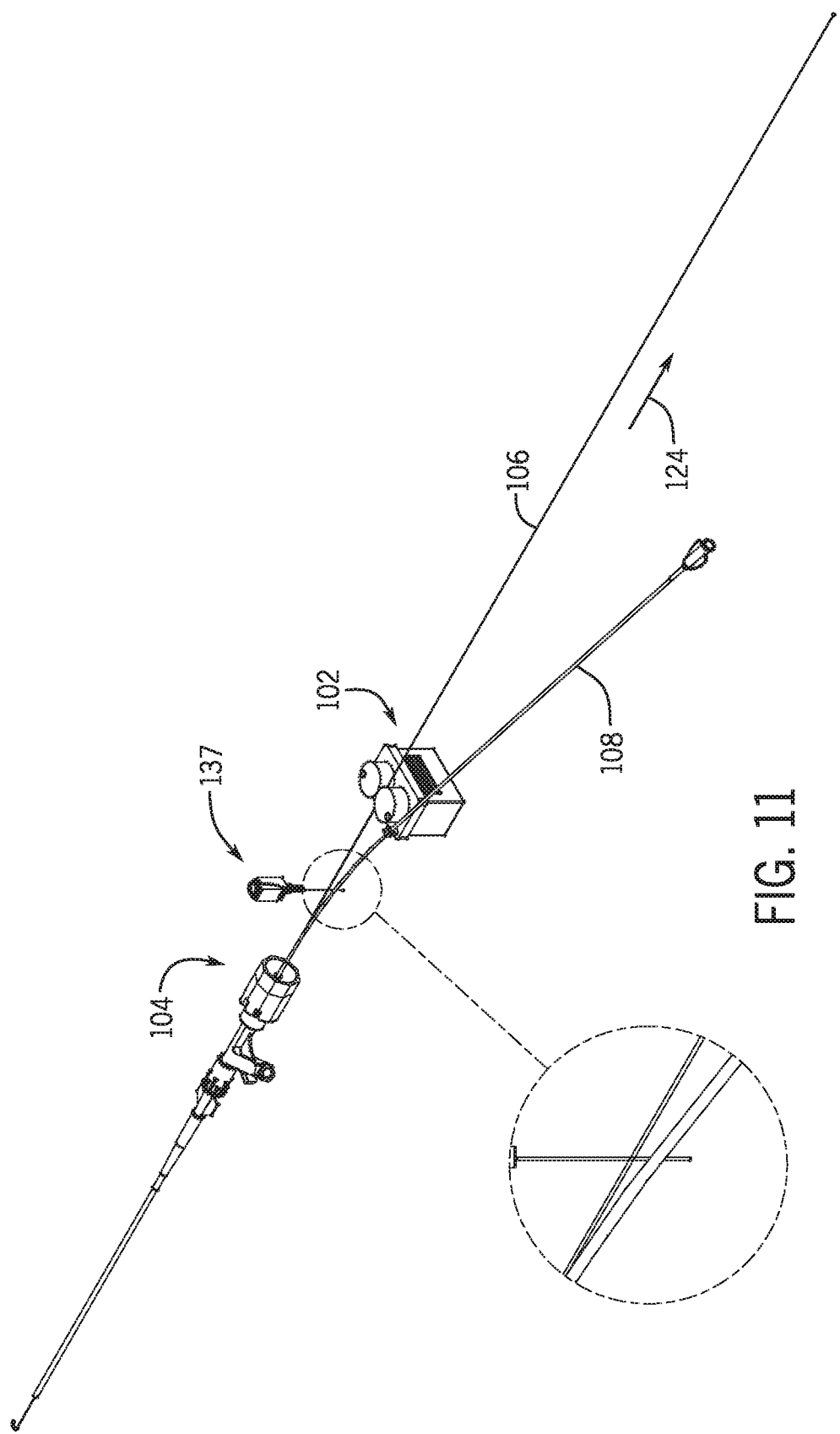
FIG. 11 is a schematic cross section of a mechanical sensor when the exchange system is in the first position.
Figure 16:
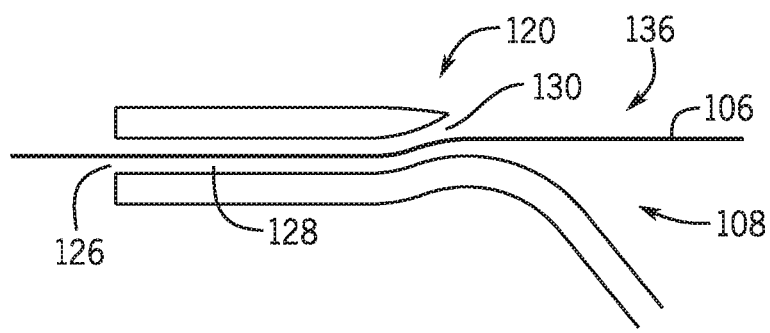
FIG. 16 is a partial cross-sectional view of a rapid exchange catheter and guidewire.
Figure 17:
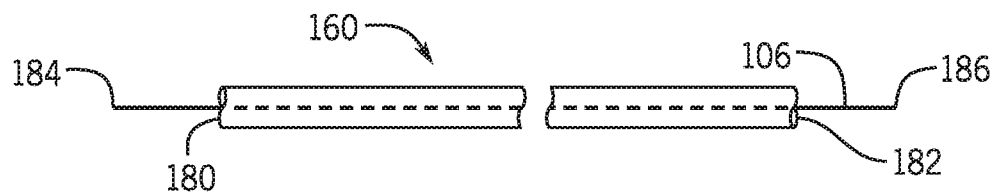
FIG. 17 is a schematic view of an over the wire catheter and guidewire.

A proximity sensor 132 positioned near the proximal end 134 of y-connector 104 detects when the proximal end 136 of the monorail portion emerges from the y-connector. Proximity sensor 132 may be a mechanical, electro mechanical, or image sensor such as a camera that coupled with hardware or computer software code determines that the proximal end of the monorail portion 120 of percutaneous device 108 has cleared the proximal end of the y-connector and/or hemostasis valve. Referring to FIG. 11 a mechanical proximity sensor 137 include an elongated member extending between the guidewire 106 and percutaneous device 108 between movable drive 102 and the proximal opening 130 of monorail portion 120 of percutaneous device 108. The elongated member is biased out of the way as percutaneous device 108 is moved in a direction away from hemostasis valve 104 along vector 124.

Once the proximal end of the monorail portion 120 has emerged the guidewire 106 and percutaneous device is placed within movable drive 102. A portion of percutaneous device 108 is operatively secured with a clamp 110 or other means to movable drive 102. Movable drive 102 is then robotically moved along a slide 122 or moved via a robotic arm 138 or other device that robotically moves movable drive 102 away from y-connector 104 in a direction 124. As movable drive 102 is moved in a direction 124 percutaneous device 108 is withdrawn from the vasculature as it rides over the portion of the guidewire within the monorail lumen 128. In order to maintain the distal end of the guidewire in a fixed position within the vasculature drive wheels 114, 116 are rotated in a manner such that moveable drive 102 moves along guidewire 106 and the distal end of guidewire 106 remains in a relatively fixed position within the vasculature.

Referring to FIGS. 1-5. Wheel 114 and wheel 116 rotate in opposite directions in a direction such the distal end of the guidewire remains fixed in its position while the mobile drive 102 moves in a direction 124 away from y-connector 104. The speed in which wheels rotate is related to the speed in which mobile drive moves.

In one embodiment the movement of mobile drive 102 is a constant velocity and is continuous and the rotation of wheels are also a constant rate and continuous. In one embodiment the movement of mobile drive 102 is done in a series of discrete motions and the rotation of wheels 114 and 116 are also done in a series of discrete motions. In one embodiment the rotation of wheels 114 and 116 are continuous but have a cam non-uniform diameter surface such that the contact with the guidewire is intermittent to match the discrete intermittent movement of the mobile drive 102. In one embodiment other types of drive systems for both the movement of mobile drive 102 in the direction 124 away from y-connector 104 and drive systems related to the movement of the guidewire relative to the mobile drive 102.

In one embodiment the movement of the guidewire drive relative to the mobile drive 102 imparts a positive pressure on the guidewire in the direction opposite to direction 124 as required to overcome any drag imparted to the guidewire from the movement of percutaneous device 108 as the percutaneous device is moved in the direction 124 away from the y-connector. In one embodiment guidewire drive may vary the speed of the guidewire drive elements such as the wheel 114 and 116 to move the guidewire to or from the y-connector to maintain the distal end of the guidewire in a stationary position relative to a feature such as a lesion or location within the vasculature while the percutaneous device is being withdrawn from the vasculature.

Referring to FIGS. 12A-12G in one embodiment a pair of clamps are used to fix the location of guidewire 106 as percutaneous device 108 is withdrawn from the vasculature and from y-connector 104 in a direction 124 away from the y-connector 104. Referring to FIG. 12A a first clamp 140 in a nonclamped orientation is moved along with percutaneous device 108 such that clamp 140 does not interfere with the percutaneous device proximate guidewire exit opening 130. A second clamp 142 located a distance further away from y-connector 104 is clamped to guidewire 106 to fix the location of the guidewire as percutaneous device 108 is being withdrawn such that a hub 144 of percutaneous device 108 move further away from y-connector 104 with a vector component along direction 124. moved away from y-connector 104. Referring to FIG. 12B first clamp 140 moves toward second clamp 142 in the open non-clamped position and once first clamp is proximate second clamp 142 first clamp operatively clamps onto guidewire 106 (See FIG. 12C). Second clamp 142 then unclamps from guidewire 106 and moves a distance in the direction 124 and clamps onto guidewire 106 (See FIG. 12D). First clamp 140 unclamps from guidewire 106 and moves toward second clamp 144 as percutaneous device 108 is moved further away from y-connector 104 along vector 124. This process is repeated until the distal opening 126 of monorail 120 clears y-connector 104. (See FIGS. 12E-12G).

In one embodiment first clamp 140 and second clamp 142 are located and operated on a base 146 that is robotically moved away from y-connector 104 and operatively clamps a portion of percutaneous device 108. A schematic of base 146 having a percutaneous clamp member 148 is shown in FIG. 12F. First clamp 140 and second clamp 142 are movable relative to base 146 such that the position of the guidewire remains fixed relative to the y-connector 104 and/or vasculature as base 146 is moved along vector 124.

In one embodiment first clamp 140 and second clamp 142 are supported on a separate structure that operates via a controller in communication with the movement of base 146. In one embodiment one or both of first clamp 140 and second clamp 142 are operated by a robotic arm having one degree of freedom and in one embodiment the robotic arm or arms have more than one degree of freedom.

Referring to FIG. 13A a first clamp 150 and a second clamp 152 operate to maintain guidewire 106 in a fixed position relative to y-connector 104 and/or to maintain a distal end of guidewire 106 in a set position with a vasculature. As percutaneous device 108 is withdrawn from the vasculature and y-connector 104 with a movable drive clamps 150 and 152 operate to maintain guidewire 106 in a fixed position. Referring to FIG. 13A first clamp 150 is in an open unclamped configuration in which clamp 150 is not clamping guidewire 106. Second clamp 152 is in a closed clamped configuration in which guidewire 106 is clamped thereto. Referring to FIG. 13A-13C as the proximal opening of the monorail lumen moves away from y-connector 104 and approaches first clamp 150, first clamp 150 is moved to a position beyond second clamp 152. Stated another way second clamp 152 is moved from a position in which it is intermediate second clamp 152 and y-connector 104 to a position in which second clamp 152 is intermediate first clamp 150 and y-connector 104. First clamp is then moved from the open unclamped configuration to a closed clamped configuration in which first clamp 150 clamp guidewire 106. Second clamp 150 is then moved to an open position from the closed position to unclamp second clamp 150 from guidewire 106. The leap frog movement of first clamp 150 and second clamp 152 continues until the distal end of the monorail portion clears the y-connector 104 or stated another way until the distal end of the monorail is intermediate the proximal end of the y-connector 104 and the percutaneous movable drive. In one embodiment a percutaneous movable drive 154 includes a base 156 having a clamp to secure percutaneous member 108 thereto. Base 156 may be robotically moved on a slide member or a robotic arm in a linear direction 124.

In one embodiment first clamp 150 and second clamp 152 are supported on a separate structure that operates via a controller in communication with the movement of base 156. In one embodiment one or both of first clamp 150 and second clamp 152 are operated by a robotic arm having one degree of freedom and in one embodiment the robotic arm or arms have more than one degree of freedom. In one embodiment first clamp 150 and second clamp 152 are supported on the base having a mechanical linkage to provide leap frog movement that moves the first clamp 150 and second clamp 152 in a synchronized movement as base 156 moves away from y-connector 104 in the direction along vector 124.

Referring to FIG. 4 proximity sensor 132 detects that the distal end of percutaneous device 108 has cleared the proximal end of y-connector 104 and sends a signal to a controller. Controller sends a signal to a proximal clamp 118 to clamp onto guidewire 106 between the distal end 126 of percutaneous device 108 and y-connector 104. In one embodiment y-connector includes a robotically controlled homeostasis valve that is activated to clamp onto guidewire 106 with sufficient force to maintain the position of the guidewire to the hemostasis valve as the percutaneous device 108 is removed completely from guidewire 106. Once proximal clamp 118 clamps onto guidewire 106, the wheels 114 and 116 release guidewire 106 and drive 102 continues to move along a path to remove the mono rail portion 120 off of the proximal end of guidewire 106. Once percutaneous device 108 has been removed from guidewire 106 it is possible to then guide a second percutaneous device 108 onto the proximal end of guidewire 106 either manually or robotically as described herein below.

In one embodiment, the first percutaneous device is removed from the guidewire robotically while the distal end of the guidewire is maintained in fixed position relative to the patient. In one embodiment the robotic system monitors guidewire movement during the removal of the first percutaneous device to ensure that the distal end remains stationary relative to the lesion. Adjustments may be made to the speed of the roller wheels relative to the linear movement of the movable drive 102 to ensure the distal end of the guidewire remains fixed with respect to the lesion. The distal end of the guidewire may be monitored using an imaging system or a portion of the guidewire external to the patient may be monitored for appropriate movement either through a visual imaging system or an electrical—mechanical interface.

Although the description describes a rapid exchange percutaneous device (monorail). System 100 is contemplated to be used both for a rapid exchange monorail type system and an over the wire system.

Referring to FIG. 14 an over the wire percutaneous device 160 is secured to a clamp 162 proximal end hub 164. Clamp 162 is operatively secured to a drive 166 that moves clamp 162 and a guidewire mechanism 170. Drive 166 is moved in a direction 168 away from a y-connector and/or hemostasis valve on a slide member, robotic arm or other translation device as discussed above with respect to drive mechanism 102. Referring to FIG. 15 clamp 162 includes a clamp portion 170 that releasably clips percutaneous device 160 to clamp 162.

Monorail Detection: In one embodiment after therapy is delivered and the balloon catheter is in the guide catheter, the balloon catheter is rapidly utilizing retracted until the monorail is detected as it exits the y-connector. In one embodiment, the monorail portion is detected, and a signal is sent to the control system for either further manual manipulation or robotic manipulation. In one embodiment balloon catheter is robotically withdrawn via a signal from the controller with a percutaneous linear drive mechanism as is known in the art. The proximal end of the monorail portion is detected utilizing a proximity sensor 132 as discussed herein above. Once a proximal end of the monorail is detected in order to avoid damage to the balloon catheter the controller sends a signal to the percutaneous linear drive mechanism to stop so that that the guidewire and balloon catheter may be switched to the movable drive 102 as discussed above.

Proximal Dynamic Guidewire Fixation: In one embodiment, the guidewire is continuously held proximal to the balloon catheter's monorail while the monorail is advanced into or retracted from the y-connector and/or hemostasis valve. This arrangement is in place whenever the distal guidewire clamp would interfere with the balloon catheter.

Guidewire Distal Clamp: In one embodiment, a second clamp 118 is positioned on the proximal side of the y-connector (the side of the y-connector further away from the patient). The second clamp 118 operatively clamps on to the guidewire after the monorail clears the Y-connector on the proximal side. The second clamp is maintained onto the guidewire until a monorail of second percutaneous device is ready to advance into the y-connector.

Auto Backload: Proximal end of guidewire is held with respect to either the first or second percutaneous device to load one of the percutaneous devices onto the guidewire. In one embodiment a guiding structure robotically guides the monorail of the percutaneous device over the guidewire to automatically backload guidewire. The guidewire is continuously held distal to the balloon catheter distal tip while the monorail is fully advanced onto the guidewire. And/or guidewire is driven into monorail until it guidewire is past the monorail's guidewire exit port.

Motorized y-connector as described in U.S. patent application Ser. No. 15/029,115 and incorporated herein by reference in its entirety: The motorized opening and closing of the y-connector valves allow for reduced friction between the portion of the percutaneous device that is coated and the y-connector. This is to minimize any damage to the coated portion of the percutaneous device as it travels through the y-connector. This feature is in addition to fixate devices and control bleedback. Percutaneous devices with coated devices include a drug coated balloon or a drug eluting stent. The motorized opening and closing of the valve in the y-connector may be used as a clamp to secure the guidewire relative to the y-connector and/or hemostasis valve when the distal end of the percutaneous device 108 is past the proximal end of the y-connector in a direction away from patient.

Figure 19:
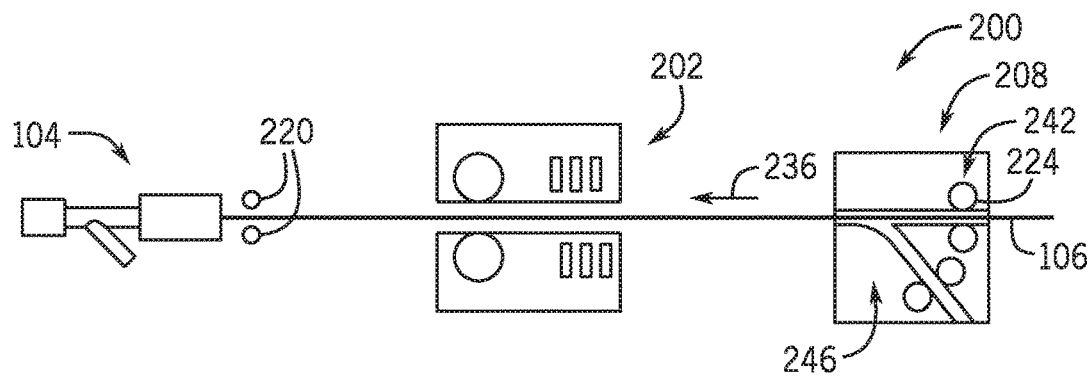
FIG. 19 is a schematic view of an exchange system with a loader in a first mode.
Figure 20:
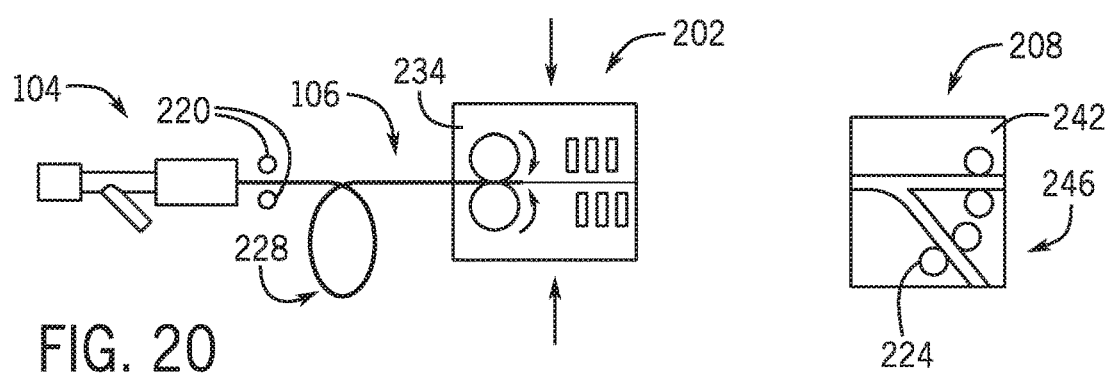
FIG. 20 is a schematic view of the exchange system with a loader in another mode.

Referring to FIG. 19 and FIG. 20 an automated percutaneous device exchange system 200 includes a loading module 202 and a drive module 208. Once a first percutaneous device 108 has been removed from the guidewire 106 a second percutaneous device 210 can be loaded onto guidewire 106. The system 200 may be used in conjunction with the system 100 as described herein above. Drive module 208 may be the same as movable drive 102 or may be the cassette drive mechanism that robotically controls the guidewire and a percutaneous device. In one embodiment a separate drive module 208 is used in the loading of the second percutaneous device 210 onto a guidewire. However, it is also contemplated that system 200 is used to load a first percutaneous drive member onto the guidewire as well. Once the first catheter or percutaneous device 108 is removed from guidewire 106, the proximal end of the guidewire is positioned within loading module 202. Loading module 202 is moved into a position between the proximal end of the guidewire and the hemostasis valve 104. As discussed herein below loading module may be formed from two components that move toward and away from one another to capture a portion of guidewire 106 within a drive mechanism 230. A clamp member 220 secures a portion of the guidewire proximal the hemostasis valve to fix the location of the distal end of the guidewire relative to one of a position with a vasculature, a patient, a patient bed, introducer, or the earth. As discussed above clamp member 232 may be the same as clamp member 118 or may be the robotic closing of the hemostasis valve.

Loading module 202 includes a guidewire drive 234 that operatively moves guidewire 106 along a vector 236. In one embodiment guidewire drive 234 includes a pair of roller members such as wheels that are robotically rotated to move guidewire 106 toward hemostasis valve 104. As guidewire 106 is moved toward hemostasis valve 104 a portion 228 of the guidewire 106 will need to be managed in a non-linear manner. In one embodiment the portion 228 of the guidewire 106 will be coiled. In one embodiment portion 228 may be robotically moved such that portion 228 forms a u-shaped loop. guidewire 106 is moved toward hemostasis valve 104 until a proximal end of the guidewire 106 is positioned within loading module 202.

Figure 21:
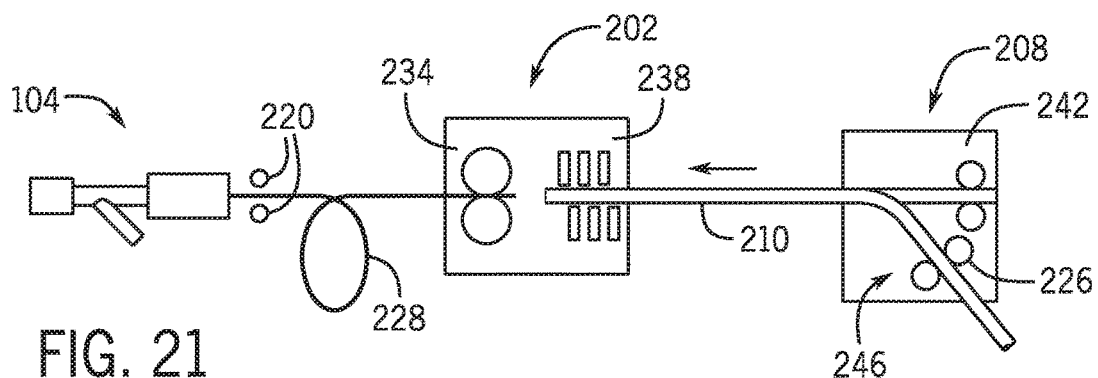
FIG. 21 is a schematic view of the exchange system with a loader in another mode.

Referring to FIG. 21 automated percutaneous device exchange system 200 includes a loading module 202 that supports a distal end of a percutaneous device 210 and threads the proximal end of a guidewire 106 into the monorail portion of percutaneous device 210. Clamp 220 pinches a portion of guidewire 106 on the proximal side of the y-connector 104. After loading module 202 moves into place a proximal end of guidewire 106 is thread into loading module 202. A pair of wheels robotically drive the proximal end of guidewire 106 in a direction away from y-connector 206. In the initial loading position a drive module 208 is positioned away from the loading module 202. The guidewire proximal tip is positioned to a known location within loading module 202 so that the tip is aligned to be inserted into the monorail portion of the percutaneous device.

Figure 23:
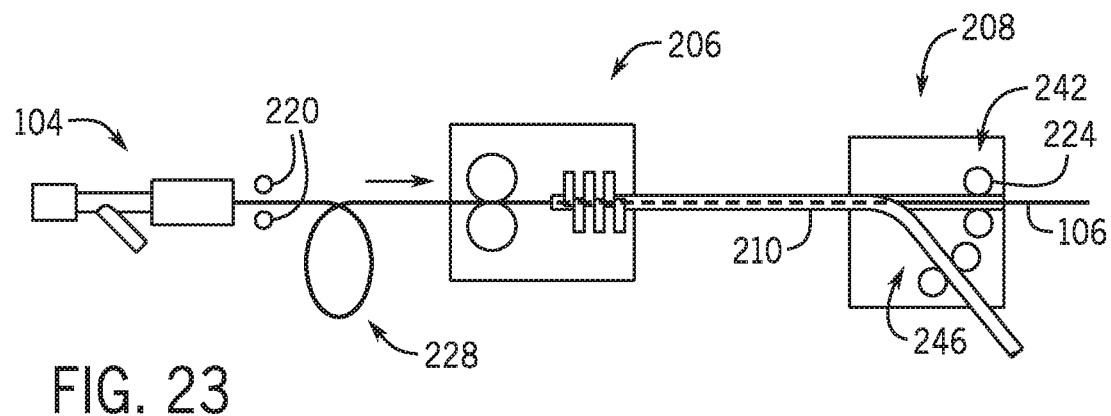
FIG. 23 is a schematic view of the exchange system with a loader in another mode.

Referring to FIG. 23 the percutaneous device 210, which as illustrated is a balloon/stent catheter is loaded into loading module 202 such that the distal end of the monorail is adjacent the proximal end of the guidewire. The percutaneous device 210 is then clamped in both the loading module 202 and the drive module 208. Referring to FIG. 23 the loading module 202 drive wheels 218 drive the guidewire proximal tip through the monorail portion of the percutaneous device 210. Magnets may assist maintaining the guidewire on the correct path as it exits the monorail portion of the percutaneous device.

Figure 24:
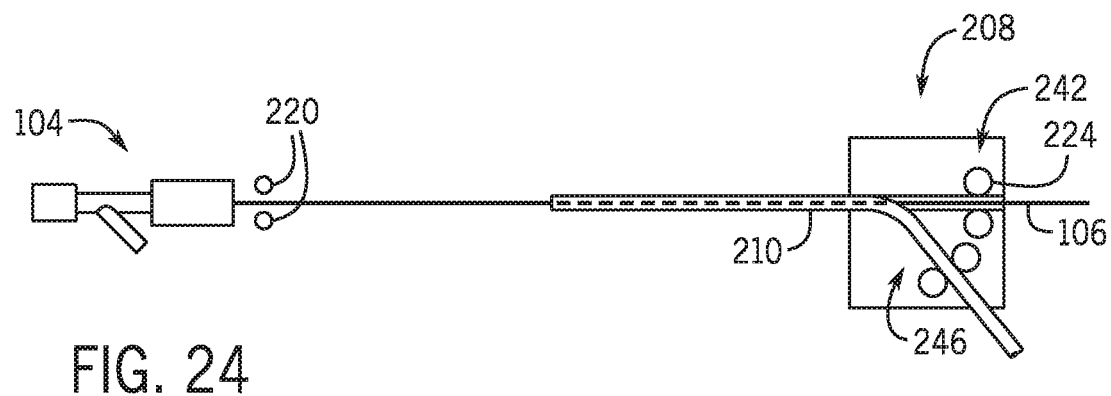
FIG. 24 is a schematic view of the exchange system with a loader in another mode.

Referring to FIG. 24 loading module 202 releases the percutaneous device 210 and the guidewire 106 and moves out of the way so that drive module 208 may move toward the y-connector. As explained above with respect to FIG. 1 and FIG. 2 drive wheels 224 on the drive module 102 maintain the guidewire 106 in a fixed location with respect to the patient as the drive module moves toward the y-connector. In one embodiment drive module 102 may be replaced with drive module 208 having a pair of wheels 226 act to both clamp the percutaneous device to the drive module 208 as well as to drive the percutaneous device into and out of the y-connector and patient.

Figure 25:
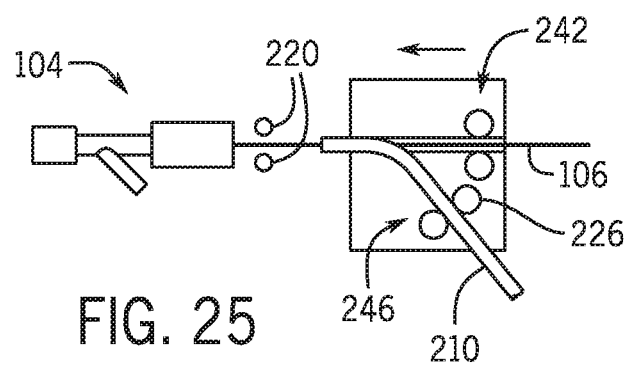
FIG. 25 is a schematic view of the exchange system with a loader in another mode.

Referring to FIG. 25 the drive module 208 is adjacent the y-connector and operates to provide axial drive of both the percutaneous device and the guidewire.

Figure 22:
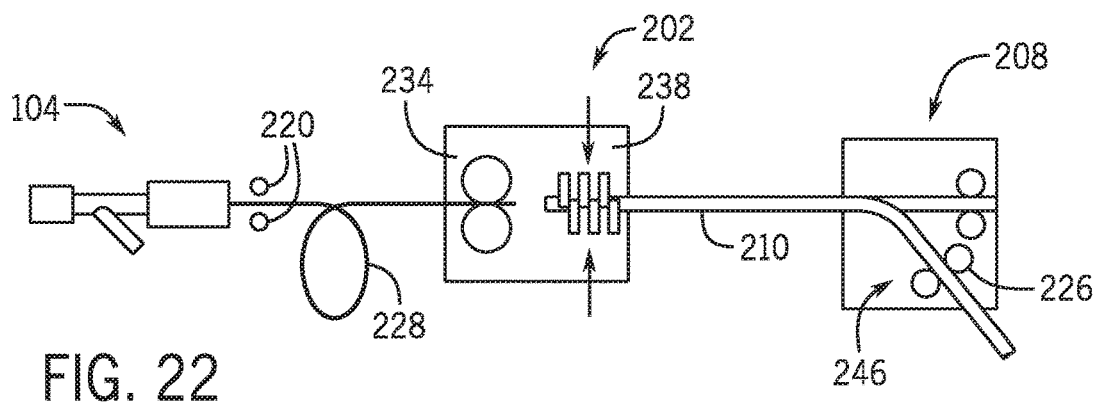
FIG. 22 is a schematic view of the exchange system with a loader in another mode.

Referring to FIG. 21 loading module 202 includes a percutaneous device locator 238 that will be described in further detail below. The distal end 240 of percutaneous device 210 is moved into device locator 238 by movement of drive module 208 toward loading module 202. In one embodiment device locator 238 is in an open configuration as distal end 240 is moved into loading module 202. Referring to FIG. 22 once distal end 240 is in a loading position device location 238 moves to the closed configuration to hold and align percutaneous device 210. Referring to FIG. 23 once the proximal end of the guidewire 106 and the distal end of the percutaneous device 210 are properly aligned guidewire 106 is inserted into a lumen of percutaneous device 210 by guidewire drive 234. In one embodiment the proximal end of guidewire 106 enters into and extends through drive module 208. Referring to FIG. 24 once portion 228 of guidewire 106 is back to a linear path drive module 208 moves toward hemostasis valve 104 loading module 206 is moved from the path between drive module 208 and hemostasis valve 104. Referring to FIG. 25 drive module 208 includes a guidewire drive 242 that operates to maintain guidewire 106 in a fixed location as drive module 208 moves towards hemostasis valve 104. In this manner percutaneous device 210 is moved along guidewire 106.

Figure 26:
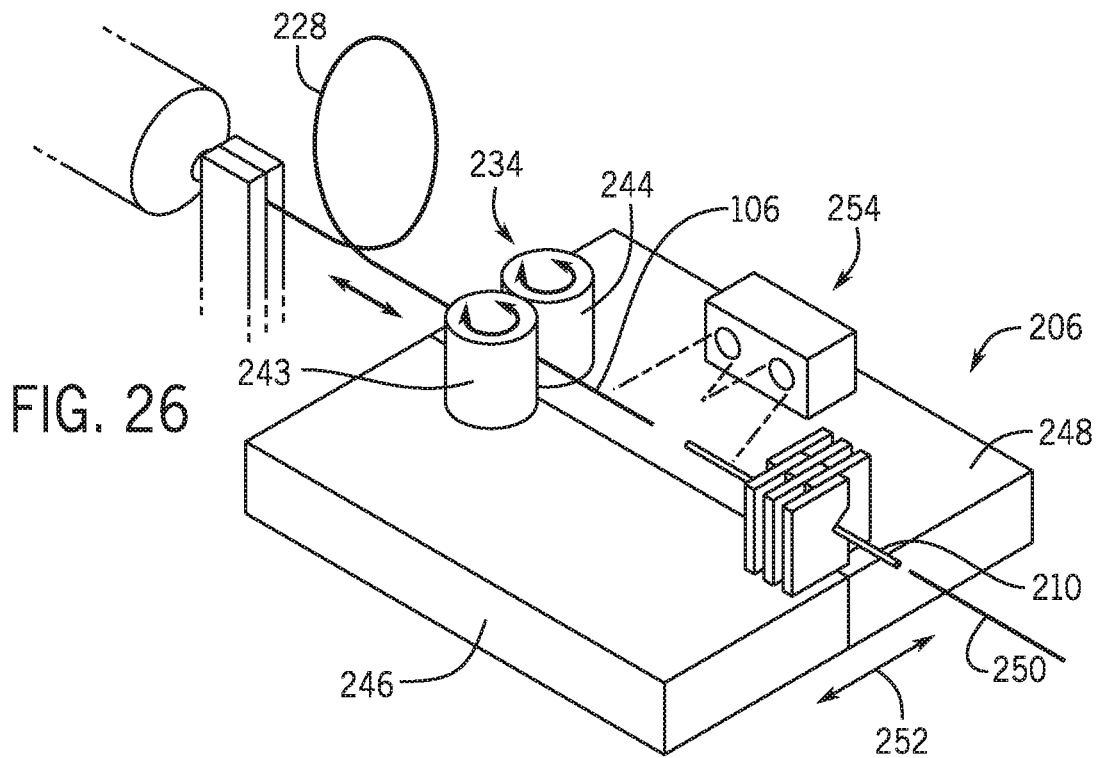
FIG. 26 is a schematic view of the loader of the exchange system of FIG. 19.

Referring to FIG. 26 loading module 206 includes a guidewire drive 234 include a pair of roller wheels 243, 244 that operatively drive guidewire 106 toward and away from hemostasis valve 104. In one embodiment loading module 206 includes a base 245 formed from a first portion 246 and a second portion 248 that move toward and away from one another. In one embodiment first and second portion 246, 248 moves along a vector 252 substantially perpendicular to a longitudinal axis 250 of hemostasis valve 104 and a portion of guidewire 106. A first wheel 243 is positioned on first portion 246 and second wheel 244 is positioned on second portion 248. In one embodiment one of wheels 246, 248 is a drive wheel that is robotically controlled by a controller in a remote control station. guidewire drive 234 drives proximal end of guidewire 106 into the distal opening of the guidewire receiving lumen of percutaneous device 210.

Percutaneous device is positioned within device locator 238. In one embodiment device locator 238 forms a channel to positively position the percutaneous device 210 such that the distal opening of the guidewire lumen is positioned to receive the proximal end of the guidewire. In one embodiment a longitudinal axis of the distal portion of the guidewire lumen and a longitudinal axis of the proximal portion of the guidewire are coaxial. In one embodiment the longitudinal axis of the distal portion of the guidewire lumen and the longitudinal axis of the proximal portion of the guidewire are at an obtuse angle relative to one another to assist in inserting the proximal end of the guidewire into the distal opening of the guidewire lumen of the percutaneous device 210 as is known in the art.

In one embodiment device location 238 includes a plurality of locating members 260 that operate to positively position the distal portion of the percutaneous device in a fixed position relative to base 245. In one embodiment a number of locating members 260 are positioned on first portion 246 and a number of locating members are positioned on second portion 248. Referring to FIGS. 27-29 and 30 locating members each include a locating feature 262 such as a recess that positively positions the longitudinal axis of the distal portion of the percutaneous device relative to base 245. In one embodiment a first group of locating members 260 and a second group of locating members are moved toward and away from one another with a rack and pinion mechanism to form a channel that positively receives and positions the distal portion of the percutaneous device.

Figure 27:
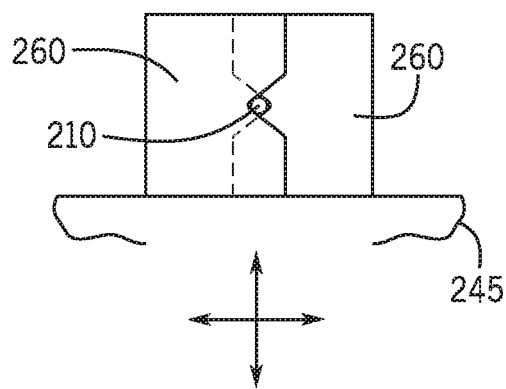
FIG. 27 is a schematic view of locator members.
Figure 28:
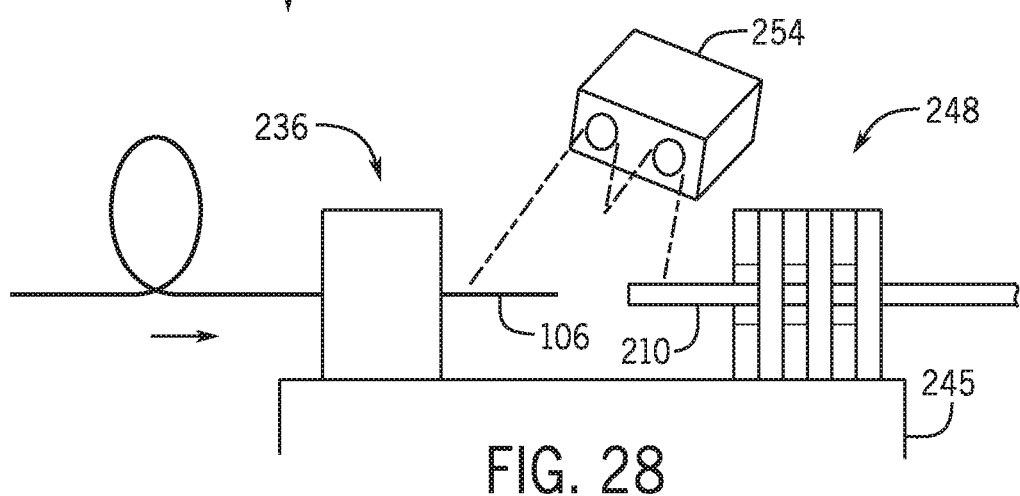
FIG. 28 is a schematic view of the loader of the exchange system with a sensor.
Figure 29:
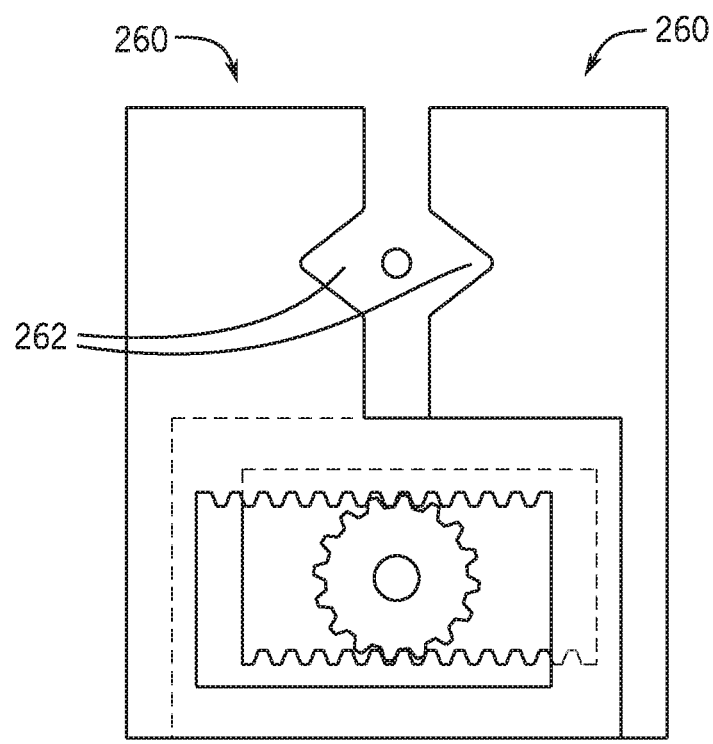
FIG. 29 is a cross sectional view of the locator members and actuating mechanism in a first position.
Figure 30:
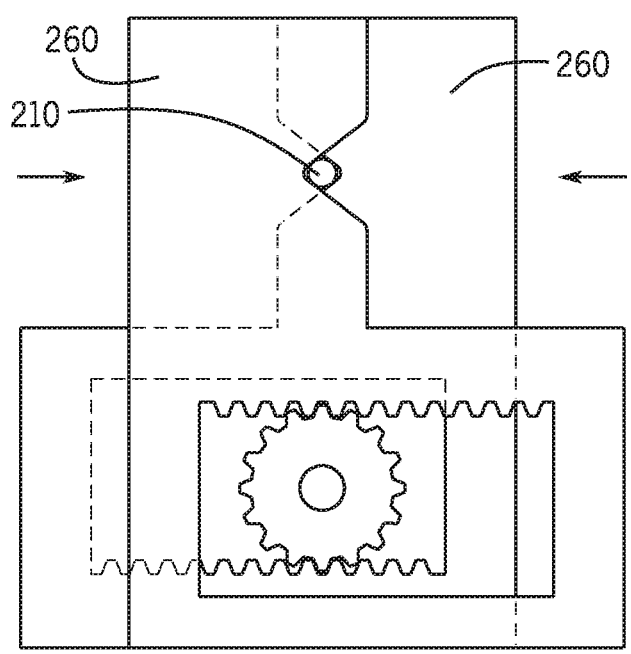
FIG. 30 is a cross sectional view of the locator members and actuating mechanism in a second position.

Referring to FIG. 27 and FIG. 28 In one embodiment a sensor 254 detects the location of the proximal tip of guidewire 106 and the distal end of percutaneous device 210. In one embodiment sensor 254 is a camera operatively coupled to an imaging system to identify the relative locations of the proximal end of the guidewire and the distal end of the percutaneous device and or more specifically to the opening to the guidewire lumen of the percutaneous device. It is also contemplated that sensor 254 be one of a magnetic sensor, inductive sensor, ultrasound sensor, tactile sensor or other sensors known in the art. In one embodiment a controller send a control signal to at least one operatively connected to members 260 to move members 260 based on an offset of the proximal end of guidewire and the distal end of the percutaneous device. In one embodiment members 260 are moved in at least two degrees of freedom. Referring to FIG. 26 and FIG. 28 sensor 254 may be mounted on base 245 or may be supported in a position by a holder other than base 245. In one embodiment sensor 254 is a 3-d sensor to identify the proximal end of the guidewire and the distal end of the percutaneous device in three dimensional space. In one embodiment percutaneous device 210 has more than one lumen opening proximate the distal end of the percutaneous device and sensor 254 identifies the guidewire lumen opening and the controller directs the motor or motors to align the proximal end of the guidewire with the guidewire lumen opening of the percutaneous device.

Figure 31:
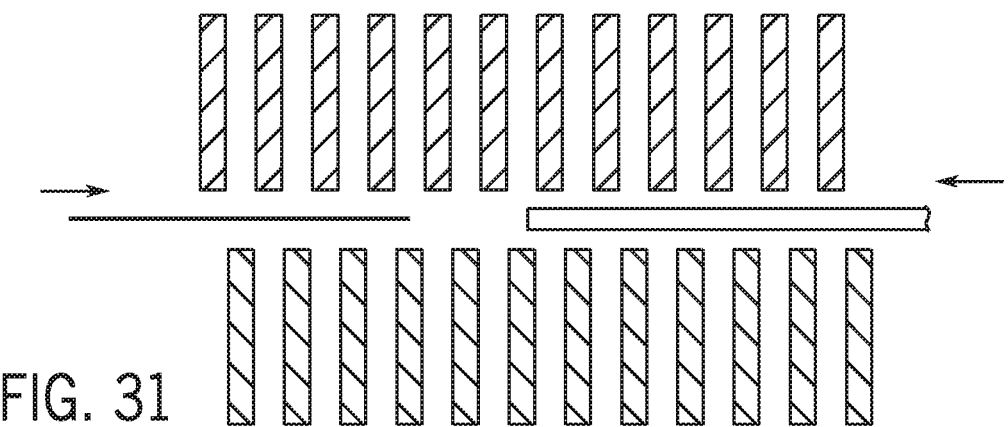
FIG. 31 is a cross sectional view of the locator members in an open position.
Figure 32:
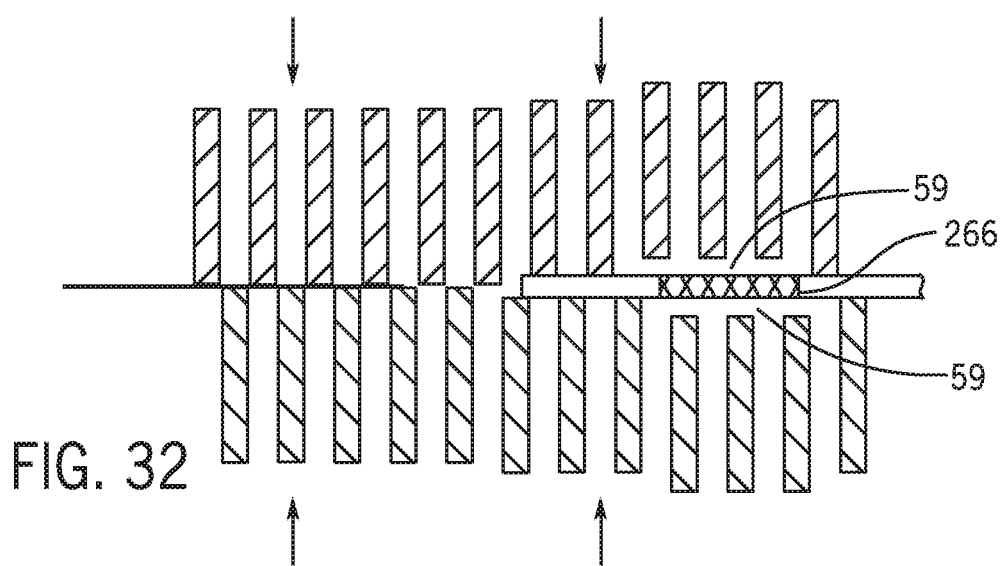
FIG. 32 is a cross sectional view of the locator members in an engaged position.

Referring to FIGS. 31 and 32 the first group of members and the second group of members in a first position are separated by a distance to allow the placement of the guidewire and percutaneous device therebetween. Once the sensor detects the proper position of the guidewire and percutaneous device along at least one direction the members are moved toward one another to positively locate the proximal end of the guidewire with the distal opening of the guidewire lumen of the percutaneous device. In one embodiment members are used to position both the guidewire 106 and catheter 210. A first channel is formed by a first group of members 260 for positioning the guidewire and a second channel is formed by a second group of members 260 for positioning the catheter. In one embodiment certain members 260 form a third channel region 59 that does not contact a portion of the catheter 266 having a therapeutic device such as a balloon, stent or other therapeutic materials.

Figure 33:
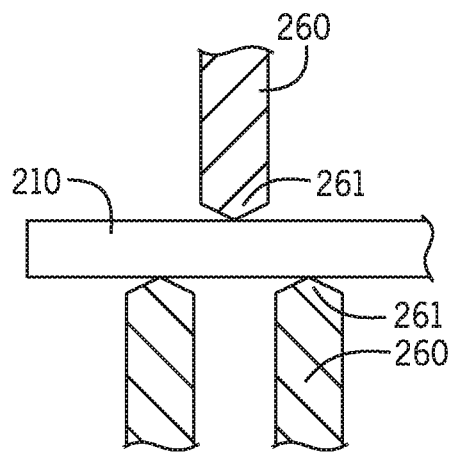
FIG. 33 is a detail view of the edge portions of the locator members in one embodiment.
Figure 34:
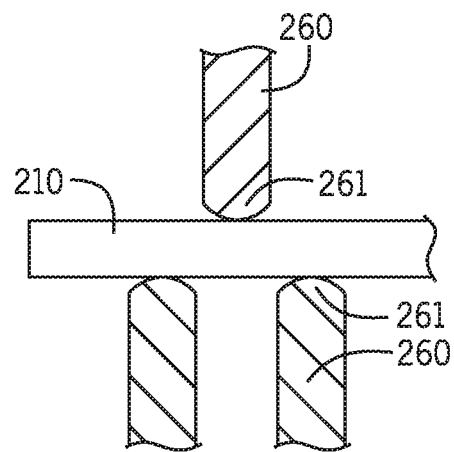
FIG. 34 is a detail view of the edge portions of the locator members in a second embodiment.

Referring to FIG. 33 and FIG. 34, the distal tips 261 of members 260 in recess 262 have a nonlinear tip. In one embodiment the shape of the tips 261 are arcuate and in one embodiment the tips converge to a vertex. In one embodiment tips 261 are formed of a softer material than the rest of members 260.

Figure 35:
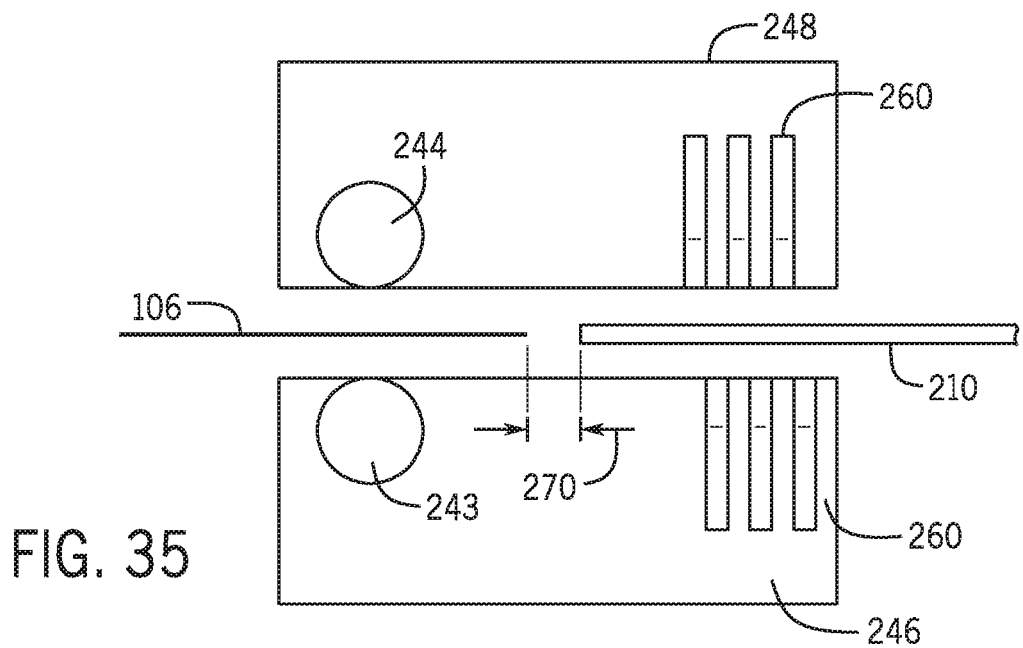
FIG. 35 is a schematic view of the loader base in an open position.
Figure 36:
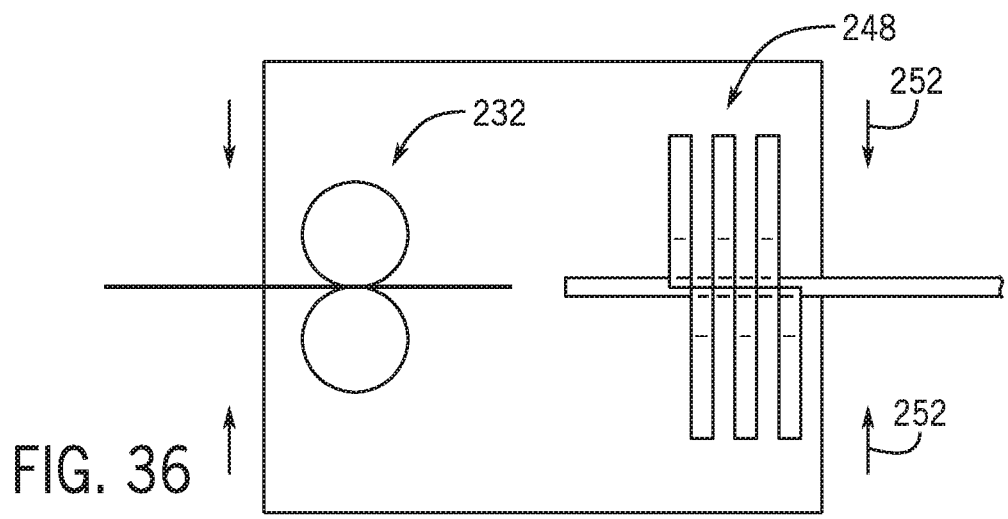
FIG. 36 is a schematic view of the loader in a closed position.
Figure 37:
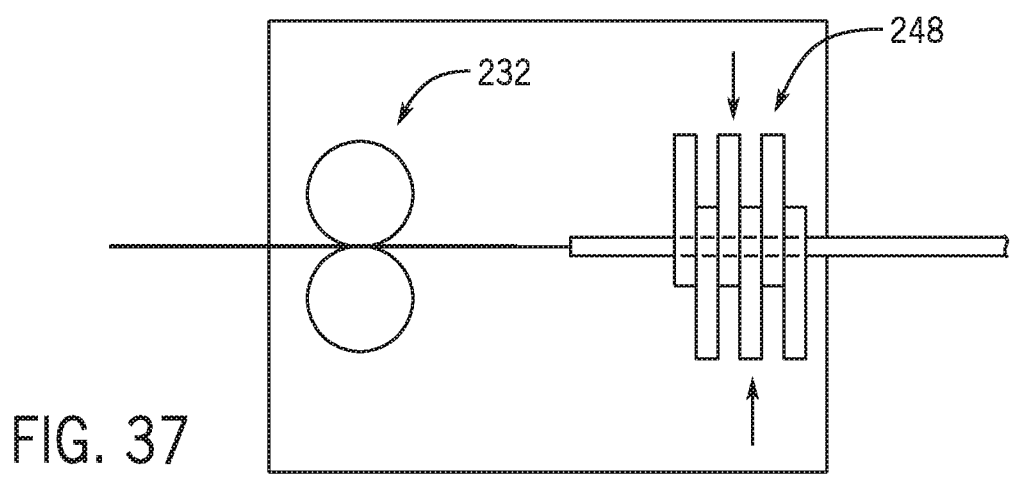
FIG. 37 is a schematic view of the loader and locator members in a closed position.

Referring to FIGS. 35 and 36 first portion 248 and second portion 246 are separate as guidewire and percutaneous device are positioned for loading. Referring to FIG. 37 once the distal end of the guidewire and the proximal end of the percutaneous device are positioned a set distance 270 from one another members 260 are then moved to a closed channel position and the distal end of the guidewire is advanced into the guidewire lumen of the percutaneous device.

Figure 38:
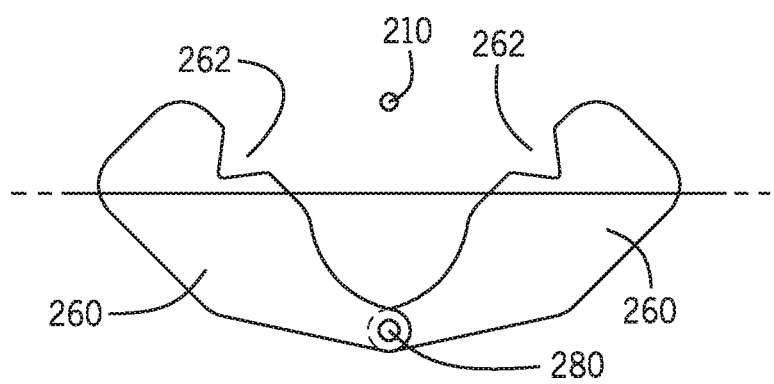
FIG. 38 is a view of locator members in an open position.
Figure 39:
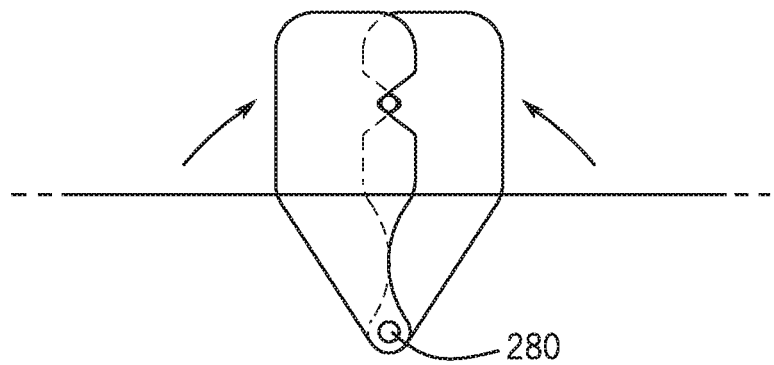
FIG. 39 is a view of the locator members of FIG. 38 in a closed position.

Referring to FIGS. 38 and 39 members 260 may be rotated relative to one another about a pivot 280 to positively position a distal portion of the percutaneous device therein to positively align the distal portion of the percutaneous device with the proximal end of the guidewire. In one embodiment locator members may be controlled separately or in groups to provide different channel gaps therebetween to accommodate different size percutaneous devices and to accommodate different outer diameters of portions of the percutaneous devices such as a balloon or stent. In one embodiment a subset of the locator members 260 provide a larger diameter channel proximate a sensitive portion of the percutaneous device such as a stent, balloon, or other therapeutic element 266.

In one embodiment a system for removing a catheter from a percutaneous device includes a hemostasis valve, and a base having a clamp releasably coupling a catheter to the base. A base drive member moves the base relative to the hemostasis valve along a first path. A mechanism maintains the position of the percutaneous device relative to the hemostasis valve while the catheter is being moved in along the first path. The term hemostasis valve includes but is not limited to a hemostasis valve that is part of an introducer sheath, a removable hemostasis valve adapter, a hemostasis valve Y-connector, a touhy-borst hemostasis valve and other hemostasis valves known in the art. In one embodiment the catheter is received directly within the hemostasis valve with no second catheter device extending about the catheter and the hemostasis valve. Or stated another way the catheter is directly in the hemostasis valve where catheter is not positioned within a guide catheter that extends through an introducer sheath's hemostasis valve.

In an example where a balloon catheter is not directly in the hemostasis valve the balloon catheter is a lumen of a guide catheter and the guide catheter goes through the hemostasis valve. In one embodiment the elongated medical device is a guidewire, but other percutaneous devices are contemplated. In one embodiment at least a portion of the first path is linear. In one embodiment at least a portion of the first path is non-linear.

In one embodiment the catheter is a guide catheter and the elongated medical device is a guidewire and the hemostasis valve is connected to the introducer sheath.

It is contemplated that holding mechanism 110 acts as a clamp to releasably couples catheter 108. It is also contemplated in one embodiment holding mechanism 110 may include a linear drive member that functions to releasably couple catheter 108 therein in addition to linearly driving catheter 108 along the longitudinal axis of the catheter. The longitudinal axis of the catheter is defined as the path through a center portion of the catheter.

It is contemplated that in one embodiment an integrated exchange system includes the unloading mechanism illustrated in FIGS. 1-18 and the loader discussed herein above and illustrated in FIGS. 19-39. Further it is contemplated that a robotic drive of a guidewire, elongated medical device such as a catheter and a guide catheter may be robotically operated in conjunction with loading and unloading mechanisms together or separately and controlled via a controller at a remote work station. In one embodiment the catheter loading and catheter unloading devices as discussed herein may move independently between an in-use and non-use position as required to allow proper functioning of all systems.

Although the present disclosure has been described with reference to example embodiments, workers skilled in the art will recognize that changes may be made in form and detail without departing from the spirit and scope of the defined subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described is manifestly intended to be as broad as possible. For example, unless specifically otherwise noted, the definitions reciting a single particular element also encompass a plurality of such particular elements.

What is claimed is:

1. An apparatus comprising:
   a hemostasis valve to receive a portion of a catheter defining a lumen;
   a base comprising a device to releasably hold the catheter to the base;
   a base drive member to move the base relative to the hemostasis valve along a first path while the catheter is held to the base such that the catheter moves relative to the hemostasis valve; and
   a mechanism coupled to the base to maintain a position of an elongated medical device removably positioned within the lumen relative to the hemostasis valve while the base and the mechanism are moved along the first path and the catheter is held to the base.

2. The apparatus of claim 1, wherein the first path is a direction that is substantially parallel to both a longitudinal axis of the elongated medical device and a longitudinal axis of the catheter.

3. The apparatus of claim 1, wherein a distal portion of the elongated medical device is maintained in a substantially fixed location relative to an anatomical feature within a patient as the base moves along the first path, and wherein a distance between the distal portion of the elongated medical device and the base changes as the base moves along the first path.

4. The apparatus of claim 1, wherein at least a portion of the first path is linear.

5. The apparatus of claim 1, wherein at least a portion of the first path is non-linear.

6. The apparatus of claim 1, wherein the base moves along the elongated medical device as the base moves along the first path.

7. The apparatus of claim 1, wherein the mechanism includes a discrete movement drive mechanism that moves the elongated medical device relative to the base in a series of discrete distances.

8. The apparatus of claim 1, wherein the base drive member moves the base with one or more degrees of freedom.

9. The apparatus of claim 1, wherein the base drive member is moved by a robotic arm having one or more degrees of freedom.

10. The apparatus of claim 9 wherein the robotic arm moves the base relative to an access site on a patient.

11. The apparatus of claim 9 wherein the robotic arm moves the base relative to a position on a patient bed.

12. The apparatus of claim 1, wherein the catheter is a rapid exchange device having a monorail portion defining a monorail lumen for a fixed length, the elongated medical device being movably received in the monorail lumen.

13. The apparatus of claim 1, further including a distal clamp removably clamping a portion of the elongated medical device once a distal end of a monorail portion of the catheter is between the distal clamp and the base.

14. The apparatus of claim 13, wherein the distal clamp is positioned between the hemostasis valve and the base.

15. The apparatus of claim 13, wherein the elongated medical device is free to move relative to the mechanism when the distal clamp clamps the elongated medical device thereto.

16. The apparatus of claim 13, wherein the elongated medical device is removed from the monorail by an elongated medical device removal drive that moves the elongated medical device through the monorail in a second direction such that a proximal end of the elongated medical device is pulled through the monorail toward the hemostasis valve.

17. The apparatus of claim 1 wherein the mechanism includes a pair of wheels to move the base relative to the elongated medical device while the base moves along the first path.

18. The apparatus of claim 1, wherein the mechanism includes a first clamp and a second clamp.

19. The apparatus of claim 18 wherein the first clamp is movable from a first position where the first clamp is intermediate the second clamp and the hemostasis valve to a second position where the second clamp is intermediate the first clamp and the hemostasis valve.

20. The apparatus of claim 1, wherein the elongated medical device is a guidewire.

21. The apparatus of claim 1, wherein the catheter is an over the wire device and the lumen extends from a proximal end to a distal end of the catheter.

22. The apparatus of claim 1, wherein a portion of the elongated medical device is maintained in a substantially fixed location relative to the hemostasis valve as the base moves along the first path, and wherein a distance between the portion of the elongated medical device and the base changes as the base moves along the first path.

23. An apparatus comprising:
a hemostasis valve to receive a portion of a catheter, wherein the catheter defines a lumen and an elongated medical device is positioned within the lumen;
a base comprising a device to hold the catheter to the base;
a base drive member to move the base relative to the hemostasis valve while the catheter is held to the base such that the catheter moves linearly relative to the hemostasis valve; and
a mechanism coupled to the base to maintain a position of the elongated medical device relative to the hemostasis valve while the base and the mechanism are moved relative to the hemostasis valve and the catheter is held to the base.

24. An apparatus according to claim 23, wherein the mechanism maintains a position of the elongated medical device relative to the hemostasis valve while the base is moved relative to the hemostasis valve by moving the elongated medical device away from the mechanism at a same rate at which the base is moving away from the hemostasis valve.

25. The apparatus of claim 23, wherein the mechanism includes a pair of wheels to move the base relative to the elongated medical device while the base is moved relative to the hemostasis valve and the catheter is held to the base.

26. The apparatus of claim 23, wherein the mechanism includes a first clamp and a second clamp.

27. The apparatus of claim 26, wherein the first clamp is movable from a first position where the first clamp is intermediate the second clamp and the hemostasis valve to a second position where the second clamp is intermediate the first clamp and the hemostasis valve.

28. The apparatus of claim 23, wherein a portion of the elongated medical device is maintained in a substantially fixed location relative to the hemostasis valve as the base is moved relative to the hemostasis valve and the catheter is held to the base, and wherein a distance between the portion of the elongated medical device and the base changes as the base is moved relative to the hemostasis valve and the catheter is held to the base.

* * * * *